US009078586B2

(12) United States Patent
Fukuda et al.

(10) Patent No.: US 9,078,586 B2
(45) Date of Patent: Jul. 14, 2015

(54) BODY FAT MEASUREMENT DEVICE

(75) Inventors: Hiroaki Fukuda, Haryana (IN); Jakusei Kiyosaki, Hyogo (JP); Shogo Fukushima, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 673 days.

(21) Appl. No.: 13/386,951

(22) PCT Filed: Jul. 26, 2010

(86) PCT No.: PCT/JP2010/004748
§ 371 (c)(1),
(2), (4) Date: Mar. 23, 2012

(87) PCT Pub. No.: WO2011/013345
PCT Pub. Date: Feb. 3, 2011

(65) Prior Publication Data
US 2012/0172747 A1    Jul. 5, 2012

(30) Foreign Application Priority Data

Jul. 27, 2009    (JP) .................................. 2009-174648

(51) Int. Cl.
*A61B 5/05*    (2006.01)
*A61B 5/053*    (2006.01)
(Continued)

(52) U.S. Cl.
CPC ............... *A61B 5/0537* (2013.01); *A61B 5/107* (2013.01); *A61B 5/4872* (2013.01); *A61B 5/6831* (2013.01)

(58) Field of Classification Search
CPC .... A61B 5/0537; A61B 5/107; A61B 5/6831; A61B 5/4872
USPC .................................................. 600/546–548
See application file for complete search history.

(56) References Cited

U.S. PATENT DOCUMENTS 6,473,642 B1    10/2002    Inoue et al.
6,978,170 B1    12/2005    Onda et al.
(Continued)

FOREIGN PATENT DOCUMENTS

CN        2156809        2/1994
CN        1293945        5/2001
(Continued)

OTHER PUBLICATIONS

Guido A. Rosito et al., "Pericardial Fat, Visceral Abdominal Fat, Cardiovascular Disease Risk Factors, and Vascular Calcification in a Community-Based Sample: The framingham heart study", Circulation, Jun. 22, 2008, pp. 605-613.
(Continued)

*Primary Examiner* — Max Hindenburg
*Assistant Examiner* — Jonathan M Foreman
(74) *Attorney, Agent, or Firm* — Greenblum & Bernstein, P.L.C.

(57) ABSTRACT

A body fat measurement device, including: a plurality of electrodes which contact a body surface of the subject; a current application unit which passes a current between a pair of electrodes of the plurality of electrodes; a first measurement unit which measures a voltage between another pair of electrodes, while current is passed between the pair of electrodes; a calculation unit which calculates an abdominal impedance of the subject on the basis of the voltage measured by the first measurement unit and calculates an amount of body fat of the subject; a second measurement unit which outputs a signal indicating a parameter other than the abdominal impedance; a cable in which a first core wire which connects between at least one of the current application unit and the pair of electrodes, and the first measurement unit and the other pair of electrodes, and a second core wire which connects the second measurement unit and the calculation unit are provided inside a same insulating coating; and an isolating unit which can shut off a connection between the second core wire and the calculation unit; wherein the calculation unit calculates the abdominal impedance on the basis of the voltage measured by the first measurement unit while a connection between the second core wire and the calculation unit is shut off, during measurement of the abdominal impedance.

20 Claims, 14 Drawing Sheets

(51) Int. Cl.
*A61B 5/00* (2006.01)
*A61B 5/107* (2006.01)

(56) References Cited

U.S. PATENT DOCUMENTS

| | | | |
|---|---|---|---|
| 8,095,211 B2* | 1/2012 | Tamura et al. | 600/547 |
| 2003/0158501 A1 | 8/2003 | Uchida et al. | |
| 2006/0282005 A1* | 12/2006 | Kasahara et al. | 600/547 |
| 2009/0018463 A1 | 1/2009 | Tamura et al. | |

FOREIGN PATENT DOCUMENTS

| | | |
|---|---|---|
| CN | 1390110 | 1/2003 |
| CN | 101066209 | 11/2007 |
| EP | 1731092 A1 | 12/2006 |
| EP | 1844707 A1 | 10/2007 |
| JP | 2007-151619 | 6/2007 |
| JP | 2009-11335 | 1/2009 |
| JP | 2009-254667 | 11/2009 |

OTHER PUBLICATIONS

JK Snell-Bergeon et al., "Measurement of abdominal fat by CT compared to waist circumference and BMI in explaining the presence of coronary calcium", vol. 28 of International Journal of Obesity, Dec. 31, 2004, pp. 1594-1599.
China Office action and search report, dated Nov. 11, 2013 along with a partial English translation thereof.
Extended European Search Report in EP10804098.1, issued Jan. 16, 2015.

\* cited by examiner

BODY FAT MEASUREMENT DEVICE

TECHNICAL FIELD

The present disclosure relates to a body fat measurement device, and more particularly, to a body fat measurement device of a type which performs measurement by wrapping a belt around the abdomen of a subject.

BACKGROUND ART

A body fat measurement device of a type which performs measurement by wrapping a belt around the abdomen of a subject has high measurement accuracy compared to a body fat measurement device of a built-in type, in weighing scales, or the like, and is used in periodic examinations, and the like. A visceral fat measurement device which uses this measurement method, namely, an abdominal impedance method, has been proposed before by the present applicants in Patent Document 1.

In the abdominal impedance method described in Patent Document 1, a pair of current application electrodes are placed on the front and back of the subject, more specifically, on the center of the subject's abdomen (navel) and the center of the subject's back (spine), and a current is passed in the front/rear direction through the subject's abdomen. Furthermore, a pair of voltage measurement electrodes are placed on the subject at staggered positions in the front and back of the body (the sides of the subject), and the abdominal impedance is calculated from the voltage between the voltage measurement electrodes when a uniform current is passed from the current application electrodes. An amount of visceral fat is measured from this abdominal impedance.

Moreover, in the abdominal impedance method described in Patent Document 1, the subcutaneous fat thickness is measured separately, and the amount of visceral fat is corrected by this measured subcutaneous fat thickness. By this means, the effects due to difference in the subcutaneous fat thickness are eliminated and the measurement accuracy of the amount of visceral fat is improved. In Patent Document 1, desirably, an optical sensor is used as subcutaneous fat thickness measurement means.

In this way, a sensor, or the like, for measuring parameters other than the abdominal impedance such as the subcutaneous fat thickness, are attached to the subject's body, apart from the current application electrodes and the voltage measurement electrodes. Signal wires are extracted from the electrodes and the sensor and are connected to a measurement device. A current is supplied to the current application electrodes by the measurement device, and the amount of visceral fat is measured from the voltages detected by the voltage measurement electrodes and the sensor, and the subcutaneous fat thickness.

In this way, if a sensor for measuring parameters other than the abdominal impedance is attached to a subject's body, apart from current application electrodes and voltage measurement electrodes which are used in order to measure abdominal impedance, then it is necessary to connect a large number of signal wires between the subject and the measurement device, and therefore the arrangement of the signal wiring becomes complicated, usability becomes worse, and the cost of the signal cables increases.

Therefore, from the viewpoint of usability and cost, it is desirable to connect the electrodes and sensor with the measurement device by using a multi-core cable in which a plurality of core wires are bunched together inside a single insulating coating. More specifically, it is desirable to form the core wires for the current application electrodes and the voltage measurement electrodes, and the core wire for the another measurement means, in an integrated fashion inside the same insulating coating.

In a body fat measurement device of a type which is built into weighing scales, for example, the impedance is measured, for example, between the legs of a subject standing on the scales, or between electrodes gripped by the subject's hands or in contact with the user's feet. Therefore, the impedance measurement path becomes long, as a result of which the measurement impedance becomes several hundred Ω, for example.

On the other hand, in a device which measures the amount of body fat from the abdominal impedance, the impedance is measured across a short distance between the subject's sides, and is one several hundredth of the impedance in a measurement device built into a weighing scales, while the measurement voltage is only several mV.

Therefore, if a multi-core cable is used and the core wires for the current application electrodes and the voltage measurement electrodes, and a core wire for another measurement means are bunched inside a single insulating coating, then the wire-to-wire capacitance and unwanted radiation from the core wire for the other measurement means has a great effect on the weak measurement voltage. Consequently, the accuracy of the voltage measurement declines and there is a risk that the measurement accuracy of the abdominal impedance will decline.

Patent Document 1: Japanese Patent Application Publication No. 2007-151619

Summary of the Disclosure

It is an object of the present disclosure to provide a body fat measurement device which is capable of reducing the risk of decline in the measurement accuracy of abdominal impedance, when calculating an amount of body fat from an abdominal impedance.

The body fat measurement device according to one aspect of the present disclosure is a body fat measurement device, including: a belt configured to be wrapped around an abdomen of a subject; a plurality of electrodes which are provided on the belt and configured to contact a body surface of the subject; a current application unit (or a current applier) which passes a predetermined current between a pair of electrodes of the plurality of electrodes; a first measurement unit (or a first measurer) which measures a voltage between another pair of electrodes, of the plurality of electrodes, while the current is passed between the pair of electrodes by the current application unit; a calculation unit (or a calculator) which calculates an abdominal impedance of the subject on the basis of the voltage measured by the first measurement unit and calculates an amount of body fat of the subject by using the calculated abdominal impedance; a second measurement unit (or a second measurer) which acquires a parameter other than the abdominal impedance and outputs a signal indicating the measured parameter to the calculation unit; a cable in which a first core wire which connects between at least one of the current application unit and the pair of electrodes, and the first measurement unit and the other pair of electrodes, and a second core wire which connects the second measurement unit and the calculation unit are provided inside a same insulating coating; and an isolating unit (or an isolator) which can shut off the connection between the second core wire and the calculation unit, wherein the calculation unit shuts off the connection between the second core wire and the calculation unit by the isolating unit, during measurement of the abdominal impedance, acquires the voltage measured by the first measurement unit while the connection is shut off, and calculates the abdominal impedance on the basis of the acquired voltage.

MODE FOR CARRYING OUT THE DISCLOSURE (First Embodiment)

Figure 1:
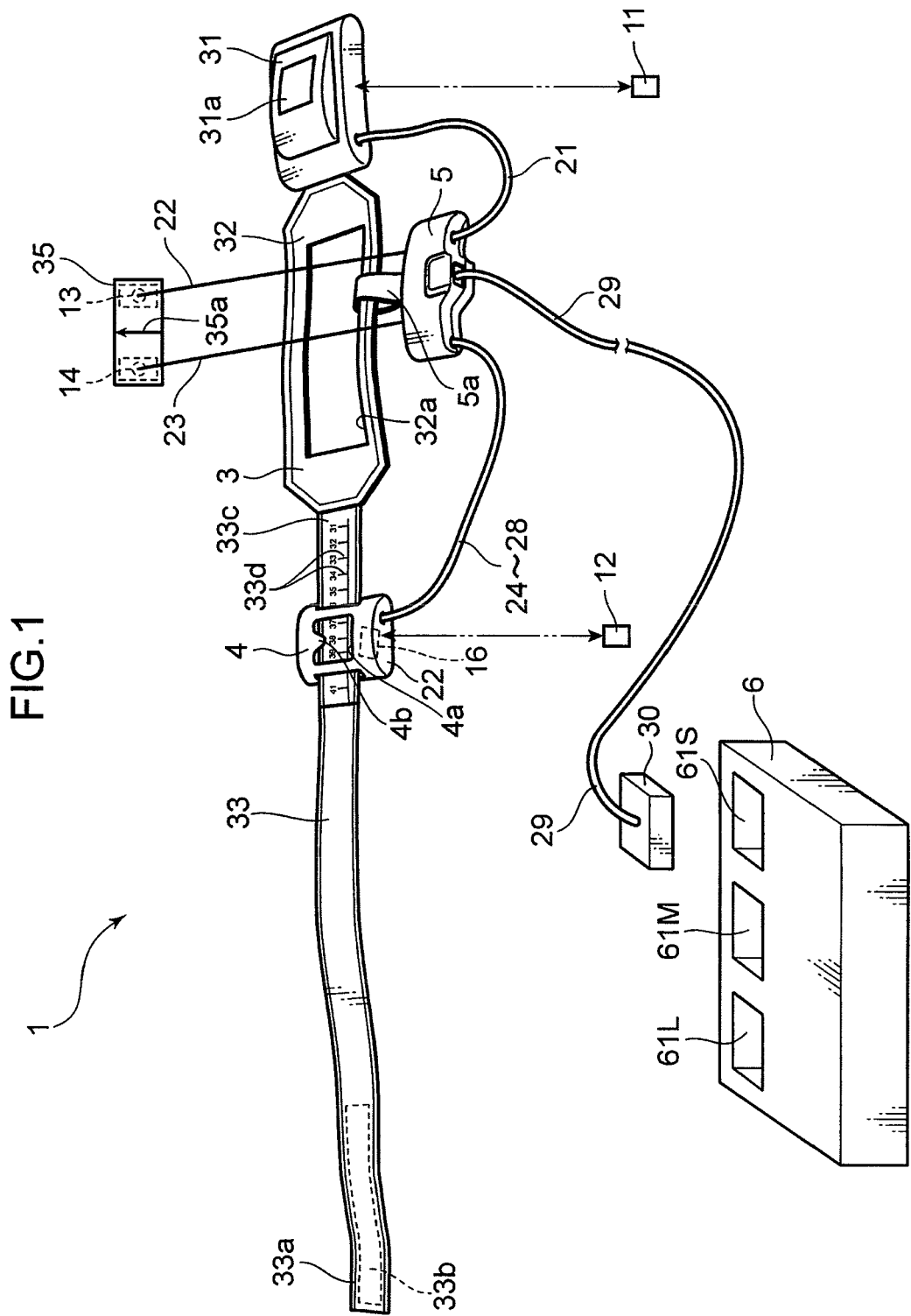
FIG. 1 is a perspective diagram of a belt-type body fat measurement device relating to one embodiment of the present disclosure.
Figure 2:
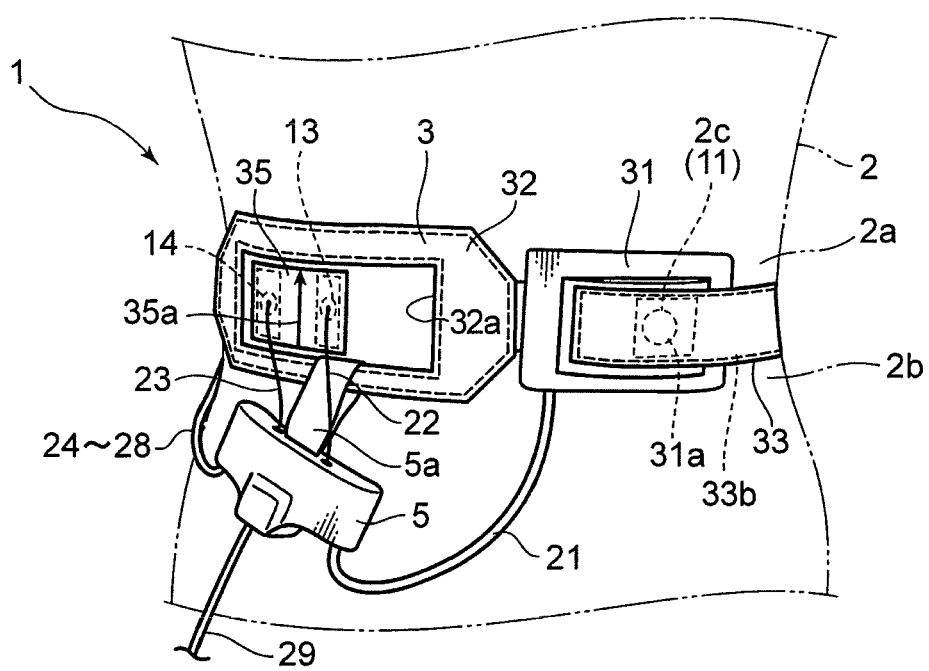
FIG. 2 is a perspective diagram showing a state of use of a body fat measurement device shown in FIG. 1.

FIG. 1 is a perspective diagram of a belt-type body fat measurement device 1 relating to one embodiment of the present disclosure. FIG. 2 is a perspective diagram showing a state of use of the body fat measurement device 1. This body fat measurement device 1 is broadly constituted by a belt 3 which is wrapped around the abdomen 2a of a subject 2, a plurality of electrodes 11 to 14 which contact the surface 2b of the abdomen 2a of the subject 2, an abdominal circumference meter 4 which is attached to the belt 3, a wire concentrator 5, and a main body 6 which is disposed separately from the belt 3. This body fat measurement device 1 is used in medical examinations, and the like, and measures the amount of body fact of a subject 2 by using an abdominal impedance method. In the body fat measurement device 1, one of, for example, three types of belt of sizes S, M and L, and equipment attached to the belts (abdominal circumference meter 4, wire concentrator 5, etc.), is selected in accordance with the waist size of the subject, and is used by connection to the common main body 6. Alternatively, respective belts 3 of different sizes and equipment attached to the belts may be connected simultaneously to the main body 6.

Figure 3:
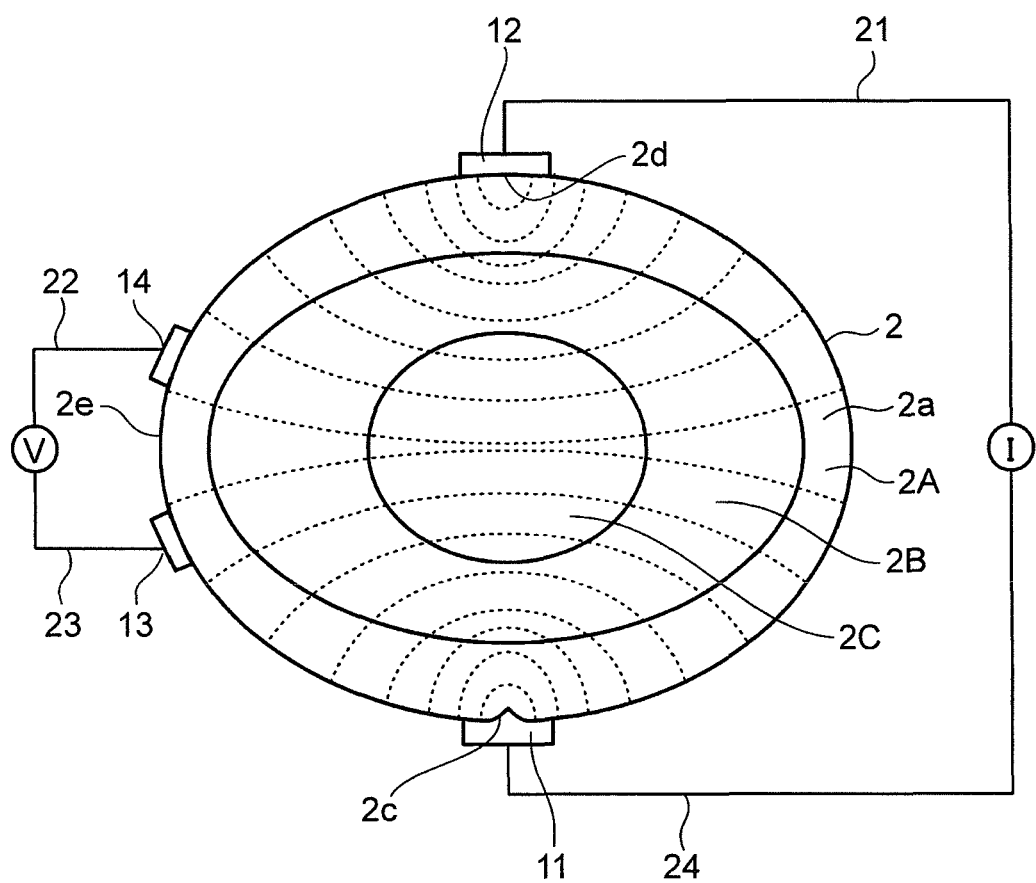
FIG. 3 is a diagram for describing the principles of measuring body fat by an impedance method.

FIG. 3 is a diagram for describing the principle of measuring body fat by the abdominal impedance method described above. To give a simple illustration, a cross-sectional view of the abdomen 2a of a person (subject 2) perpendicular to the axis (a horizontal cross-section) can be depicted as shown in FIG. 3. More specifically, inside the subcutaneous fat 2A, there is muscle tissue 2B and visceral fat 2C accumulates inside this muscle tissue 2B. Here, a pair of current application electrodes 11, 12 are provided on the center of the abdomen (navel) 2c of the subject 2 and the center of the back (spine position) 2d of the subject 2, and when a predetermined current is passed between these electrodes 11, 12, equipotential lines occur in virtual front/back symmetry in the abdomen 2a due to the passage of the current, as shown by the broken lines in FIG. 3. In this case, the ends of the equipotential lines which pass through the portion of the visceral fact 2C appear at the sides 2e of the subject 2. Therefore, when voltage detection electrodes 13, 14 are placed in contact with the front and rear of a side 2e of the subject 2, the potential difference generated in the portion of the visceral fat 2C can be detected by the voltage detection electrodes 13, 14 as a detection voltage V.

It is known that, in general terms, the product obtained by multiplying the detection voltage V by the total cross-sectional area of the abdomen 2a is proportional to the area of the visceral fat. In practice, taking the constant current that is passed to be I and taking the detection voltage to be V, then the resistance (impedance) R of the visceral fat 2C can be determined from Formula (1) below. Desirably, the resistance (impedance) R of the visceral fat 2C is read out from a previously created look-up table in association with other parameters (information) such as gender, weight, abdominal circumference, subcutaneous fat thickness, and the like, and the amount of body fat is determined by carrying out appropriate interpolation calculations, and the like. Below, the resistance (impedance) R of the visceral fat 2C is called the "abdominal impedance" R.

$$\text{Abdominal impedance } R = V/I \qquad (1)$$

More specifically, the greater the amount of visceral fat 2C, the greater the abdominal impedance R. The relationship between the abdominal impedance R and the amount of body fat varies depending on parameters indicating physical quantities, such as the subject's body weight and abdominal circumference, and parameters indicating the subject's gender.

Therefore, a look-up table which associates body fat values with combinations of various parameters, such as abdominal impedance R, gender, weight, abdominal circumference, and the like, is determined in advance by experimentation, for instance, and then stored in a memory 615 which is described below. A control microcomputer 611, also described below, then acquires various parameters such as the abdominal impedance R, gender, weight, abdominal circumference, and the like, and obtains the amount of body fat stored in association with these parameters in the look-up table stored in the memory 615, as the amount of body fat of the subject. In this way, by determining the amount of body fat using parameters other than the abdominal impedance R, in addition to the abdominal impedance R, the calculation accuracy of the amount of body fat is improved.

The look-up table is not necessarily limited to an example which associates a body fat amount with a combination of respective parameters, such as the abdominal impedance R, gender, weight, abdominal circumference, and the like. The look-up table may also associate the body fat amount with the abdominal impedance R, or may associate the body fat amount with a combination of a portion of the parameters of abdominal impedance R, gender, weight and abdominal circumference, or may include parameters other than gender, weight and abdominal circumference.

Returning to FIG. 1 and FIG. 2, therefore, the belt 3 is constituted by a base side buckle 31, a slit portion 32 connected to this, and a belt-shaped portion 33 connected to this. A surface fastener (a hook section, for example) 31a is attached to the front surface of the buckle 31, and a surface fastener (a loop section, for example) 33b which corresponds with the surface fastener 31a is attached to the rear surface of the free end 33a of the belt portion 33. By applying strong pressure to the surface fastener 31a and the surface fastener 33b, it is possible to wrap the belt 3 tightly around the abdomen 2a of a subject 2 having any girth. Here, the surface fasteners 31a and 33b are a pair of so-called mechanical fasteners consisting of hooks and loops, in which, when pressed strongly together, the hook section and loop section interlock and become difficult to separate, and when pulled strongly apart, the interlocking is released and the hook section and loop section can be peeled apart.

Figure 4:
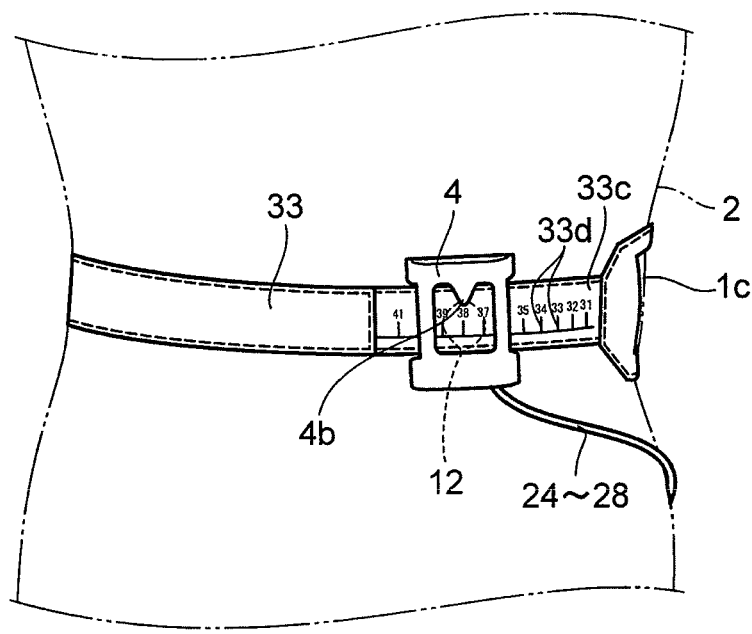
FIG. 4 is a diagram for describing a method of measuring abdominal circumference.

As shown in FIG. 2, a buckle 31 is arranged at a position of the center of the abdomen (navel) 2c on the surface 2b of the subject 2, and the belt 3 is wrapped in a clockwise direction and the surface fastener (loop section) 33b on the free end 33a is attached to the surface fastener (hook section) 31a on the buckle 31. In this way, it is possible to fix the belt 3 to the abdomen 2a of the subject 2, as shown in FIG. 2 and FIG. 4. Furthermore, by this means, the current application electrode 11 provided on the rear surface of the buckle 31 (the first current application electrode) makes contact with a position in the center of the abdomen (navel) 2c on the surface 2b of the subject 2.

The slit portion 32 connects with the buckle 31, and an electrode sheet 35 is attached to a portion of the inside of an opening 32a of the slit portion 32, which corresponds with the side 2e of the subject 2. The electrode sheet 35 is constituted by attaching voltage detection electrodes 13, 14 consisting of gel electrodes to a flexible plastic sheet coated with adhesive. Therefore, the voltage detection electrodes 13, 14 are not fixed to the belt 3, and hence it is possible to provide the voltage detection electrodes 13, 14 accurately at a position on the side 2e of the subject 2, for subjects 2 having different abdominal circumferences. Furthermore, even if the voltage detection electrodes 13, 14 are not pressed against the subject 2 by the belt 3, the voltage detection electrodes 13, 14 adhere to the subject 2 with a uniform adhesive force, and therefore stable voltage detection can be achieved.

In the belt-shaped portion 33 which connected with the slit portion 32, an abdominal circumference meter 4 is fitted into the base end 33c side. A current application electrode 12 (second current application electrode) which opposes the current application electrode 11 is provided on the rear surface of this abdominal circumference meter 4. The user, such as a subject 2 or an examination technician, wraps the belt 3 around the subject 2 as described above, and then slides the abdominal circumference meter 4 so to position the meter in the center of the abdomen, as shown in FIG. 4. By this means, it is possible to dispose the current application electrodes 11, 12 in opposing fashion on the subject 2, at the center of the abdomen (navel) 2c and at the center of the back (spine) 2d. The current application electrodes 11, 12 correspond to one example of a pair of electrodes.

Furthermore, in the belt-shaped portion 33, an indicator mark which shows the abdominal circumference by means of magnetic strips, slits, or the like, is embedded in the base end 33c side, and the abdominal circumference is measured by means of the indicator mark being read by a measuring unit 16 (see FIG. 6) which is built into the abdominal circumference meter 4. More specifically, when the current application electrode 12 has been arranged at a position at the center of the subject's back (spine) 2d, as described above, the length from the current application electrode 11 embedded in the buckle 31 to the current application electrode 12 is determined via the slit portion 32. The length A from the current application electrode 11 to the current application electrode 12 which is determined in this way is measured by means of the measuring unit 16 reading out the indicators embedded in the belt-shape portion 33. The measuring unit 16 is then able to determine the abdominal circumference by multiplying the measured length A by two.

The measuring unit 16 corresponds to one example of a second measuring unit. The second measuring unit is not limited to one which measures the abdominal circumference, and may be a unit which measures other parameters, such as the subcutaneous fat thickness, or the like.

Figure 5:
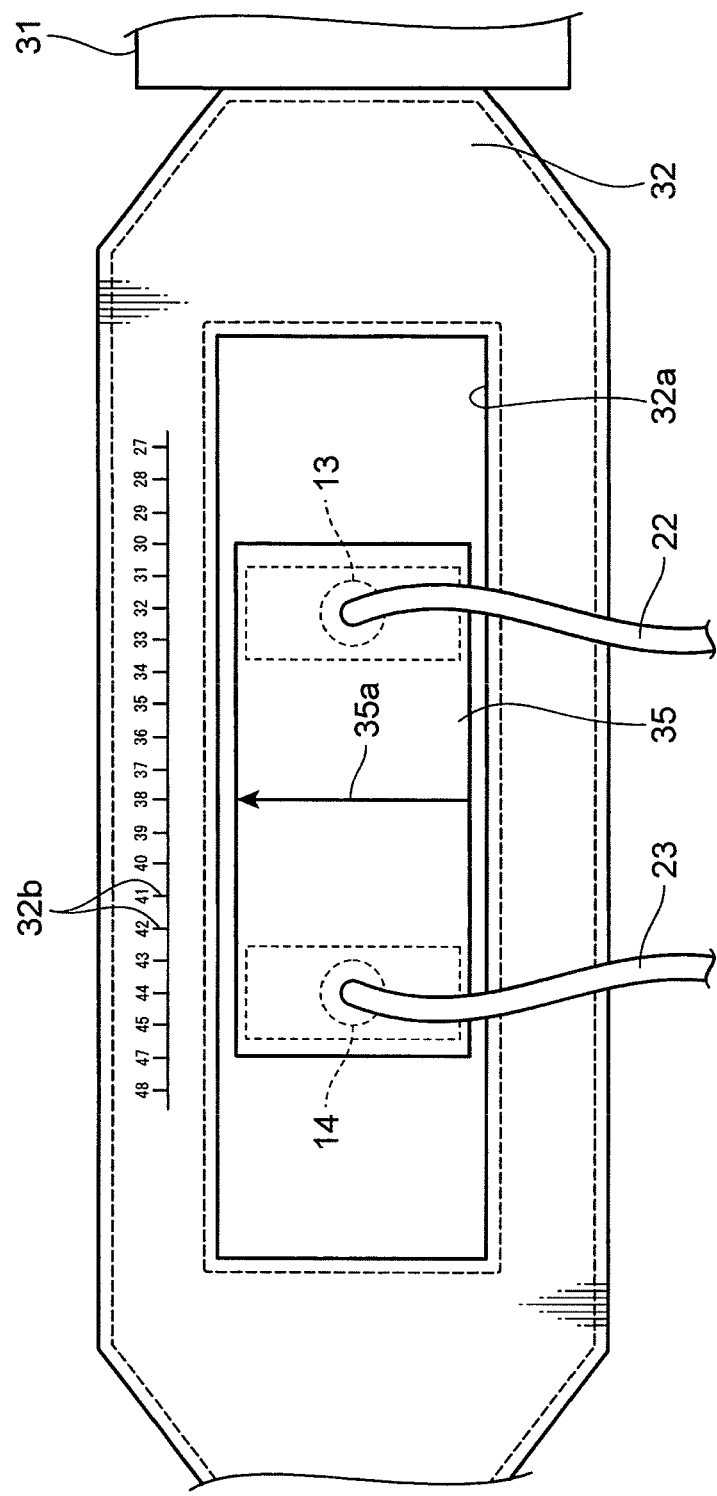
FIG. 5 is an enlarged view of FIG. 4.

Moreover, as shown in FIG. 1 and FIG. 4, an indicator mark 33d which indicates the abdominal circumference is provided visibly on the belt-shape portion 33, in such a manner that a user (technician, or the like) can measure the abdominal circumference directly. An indicator arrow 4b is also provided in an opening 4a of the abdominal circumference meter 4 through which the belt-shape portion 33 passes. In accordance with this, as depicted in enlarged view in FIG. 5, indicator marks 32b indicating the abdominal circumference are also formed in the slit portion 32. By aligning an indicator mark 35a attached to the electrode sheet 35 with the position on the indicator marks 32b of the value read out by the indicator arrow 4b of the abdominal circumference meter 4, the voltage detection electrodes 13, 14 are easily registered in position in such a manner that a prescribed position of the side 2e of the subject 2, in other words, the center between the voltage detection electrodes 13, 14 is situated at a position one half of the length from the current application electrode 11 to the current application electrode 12. The voltage detection electrodes 13, 14 correspond to one example of another pair of electrodes.

On the other hand, a wire concentrator 5 is suspended by a cord 5a from the slit portion 32. Single-core lead wires 21, 22, 23 from the current application electrode 11 and the two voltage detection electrodes 13, 14 and five-core lead wires 24, 25, 26, 27, 28 from the abdominal circumference meter 4 are connected to the wire concentrator 5 by a connector, or the like. The wire concentrator 5 concentrates these lead wires 21 to 28 into a single cable 29 with an insulating coating, and connects to the main body 6. In this way, by uniting the lead wires 21 to 28 into a single cable 29, usability is improved and costs can be reduced.

Figure 6:
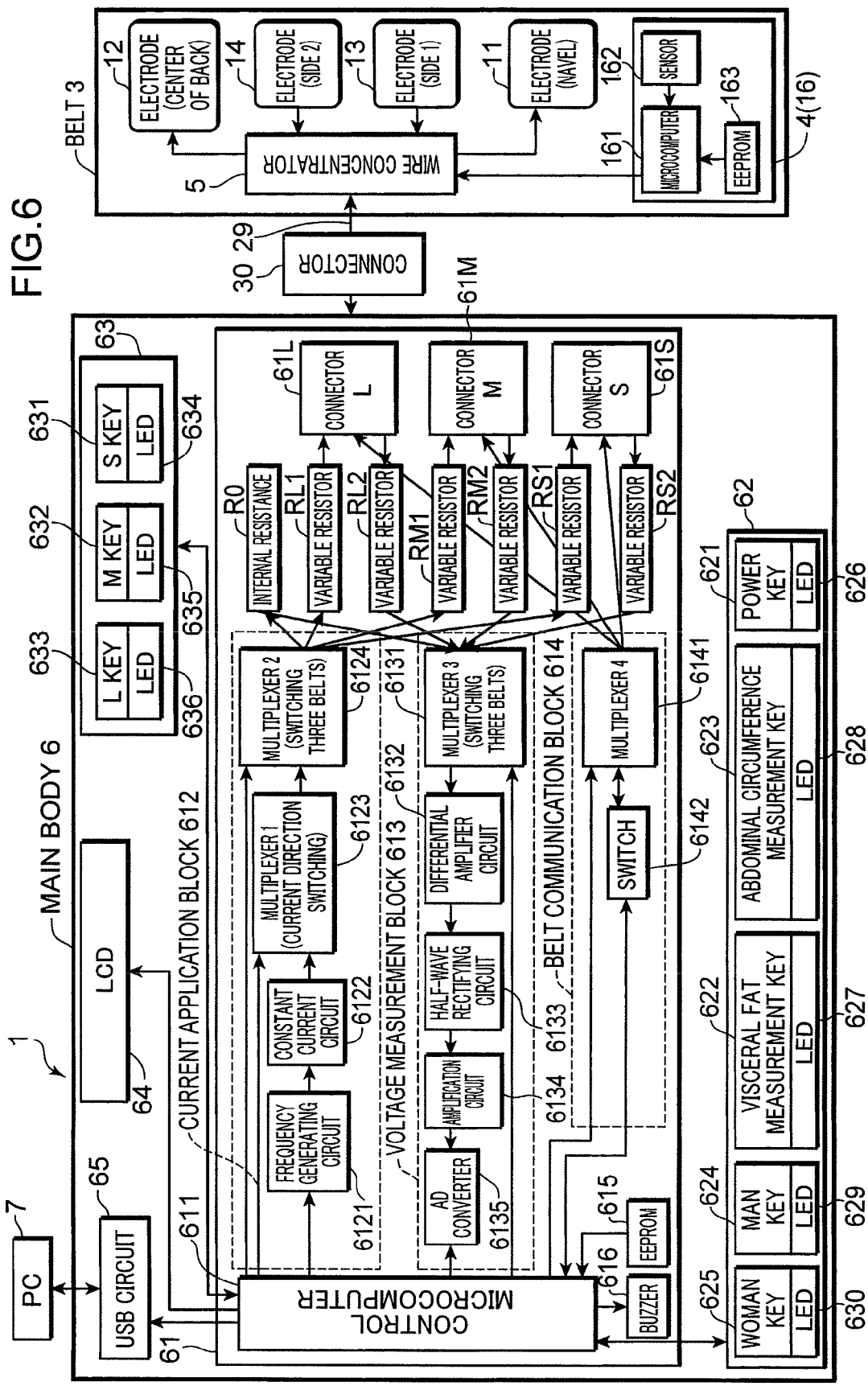
FIG. 6 is a block diagram showing an electrical composition of the body fat measurement device shown in FIG. 1.

FIG. 6 is a block diagram showing an electrical composition of the body fat measurement device 1 shown in FIG. 1. The main body 6 comprises a main board (circuit board) 61, an operation control board (circuit board) 62, a board (circuit board) 63 for selecting belts of three types of sizes S, M and L, a display panel 64, and a USB interface board (USB board) 65. The main board 61 is connected to an external personal computer 7, or the like, via a USB interface board 65. By this means, information about the amount of body fat measured by the main board 61 is sent to the personal computer 7, and measurement results can be compiled and recorded by the personal computer 7, and the detailed settings in the main board 61, and the like, can be established from the personal computer 7.

In FIG. 6, a belt 3 and equipment attached to the belt 3 are depicted. Furthermore, the belts of three types of the sizes S, M, L have a common electrical composition, and therefore the belt 3, the cable 29 and the connector 30 shown in FIG. 6 relating to each of the belts.

A power key 621, a visceral fat measurement key 622, an abdominal circumference measurement key 623 and man and woman selection keys 624, 625 are provided on the operation control board 62. Indicators (LEDs) 626 to 630 which light up respectively in response to the operation of the keys 621 to 625 are provided. Similarly, keys 631 to 633 are provided on the belt selection board 63 in order to select which of the three types of belt S, M, L is to be used in measurement. The indicators LEDs 634 to 636 light up respectively in response to the operation of the keys 631 to 633. The display panel 64 is made from a liquid crystal display device, or the like.

The main board 61 is constituted by a control microcomputer 611, a current application block 612, a voltage measurement block 613, a belt communication block 614, a memory (EEPROM) 615, a buzzer 616, variable resistors RS1, RS2, RM1, RM2, RL1, RL2, a dummy internal resistance R0, and connectors 61S, 61M, 61L.

The control microcomputer 611 corresponds to one example of a calculation unit, a contact judgment unit (or a contact determiner), an adjustment unit (or an adjuster) and a drive unit (or a drive).

The connectors 61S, 61M and 61L are provided respectively for each of the belts 3 of three types, S, M, L, and the connectors 30 provided on the ends of the cables 29 from the wire concentrators 5 of the respective belts 3 are attached respectively to the connectors 61S, 61M, 61L. The connectors 61S, 61M, 61L and the connectors 30 are formed so that, structurally, they can only be fitted into the corresponding connector. Here, in a physical examination, or the like, a large number of subjects are examined, and therefore the connectors 30 of the belts 3 of three sizes are left fitted to the respectively corresponding connectors 61S, 61M, 61L and can be selected by the keys 631 to 633, thereby increasing examination efficiency.

The connectors 61S, 61M, 61L and the connectors 30 have at least an 8-pin composition so as to correspond to the cables 29 from the wire concentrator 5, and firstly, variable resistors RS1, RM1, RL1 are connected in series to any of the lines connecting the lead wires 21, 24 to the current application electrodes 11, 12, and similarly, variable resistors RS2, RM2, RL2 are connected in series to any of the lines connecting to the lead wires 22, 23 from the voltage detection electrodes 13, 14.

The variable resistors RS1, RM1, RL1, RS2, RM2, RL2 and the control microcomputer 611 correspond to one example of a fluctuation suppression unit (or a suppressor).

On the other hand, the current application block 612 which is one example of a current application unit, is constituted by a frequency generating circuit 6121, a constant current circuit 6122, and multiplexers 6123, 6124. At the start of a visceral fat measurement operation, the control microcomputer 611 starts a frequency generating circuit 6121, and generates a pulse wave at 100 kHz, for example. In response to this pulse wave, the constant current circuit 6122 generates a corresponding alternating constant current, for example, a 1 mA constant current pulse. The current direction of this constant current pulse is set by a multiplexer 6123 to either a forward direction from the current application electrode 11 to the current application electrode 12, or a reverse direction from the current application electrode 12 to the current application electrode 11, and the constant current pulse is output to the selected belt, S, M or L, by a multiplexer 6124. The constant current pulse described above is applied between the current application electrodes 11, 12 of the selected belt via the variable resistor and connector corresponding to the selected belt, of the variable resistors RS1, RM1, RL1 and connectors 61S, 61M, 61L, and via the connector 30 and the lead wires 21, 24.

Furthermore, the voltage measurement block 613 which is one example of the first measurement unit comprises a multiplexer 6131, a differential amplification circuit 6132, a half-wave rectifying circuit 6133, an amplification circuit 6134, and an analog/digital converter 6135. The voltage detected between the voltage detection electrodes 13, 14 of the belt 3 is input to the multiplexer 6131 via the variable resistors RS2, RM2, RL2, from the lead wires 22, 23, and the connector 30 and connectors 61S, 61M, 61L, and the voltage output of the belt which is the measurement object, in other words, the detection voltage, is selected by the multiplexer 6131. The selected detection voltage is amplified by the differential amplification circuit 6132, rectified by the half-wave rectification circuit 6133, and then amplified by the amplification circuit 6134, converted to digital data by the analog/digital converter 6135, and input to the control microcomputer 611, whereby the amount of body fat can be calculated.

Moreover, the belt communication block 614 comprises a multiplexer 6141, and a switch 6142. One of the connectors 61S, 61M, 61L is selected by a switching operation of the multiplexer 6141, and the lines (connector pins) connected to the lead wires 25 to 28 in the selected connector are connected to the control microcomputer 611 via the switch 6142. By this means, the control microcomputer 611 and the control microcomputer 161 of the measurement unit 16 are able to communicate with each other via the connectors 61S, 61M, 61L, the connectors 30, and the lead wires 25 to 28. Of the lead wires 25 to 28, two wires are signal wires between the control microcomputers 611, 161, one wire is a power supply wire, and the remaining wire is a GND wire. The switch 6142 functions as an isolating unit. The switch 6142 is formed, for example, by using a plurality of transistors which are introduced respectively in series with the power wires corresponding to the lead wires 25 to 28, the GND wire and the signal wires. The transistors of the switch 6142 are switched on and off by the control microcomputer 611.

Figure 7:
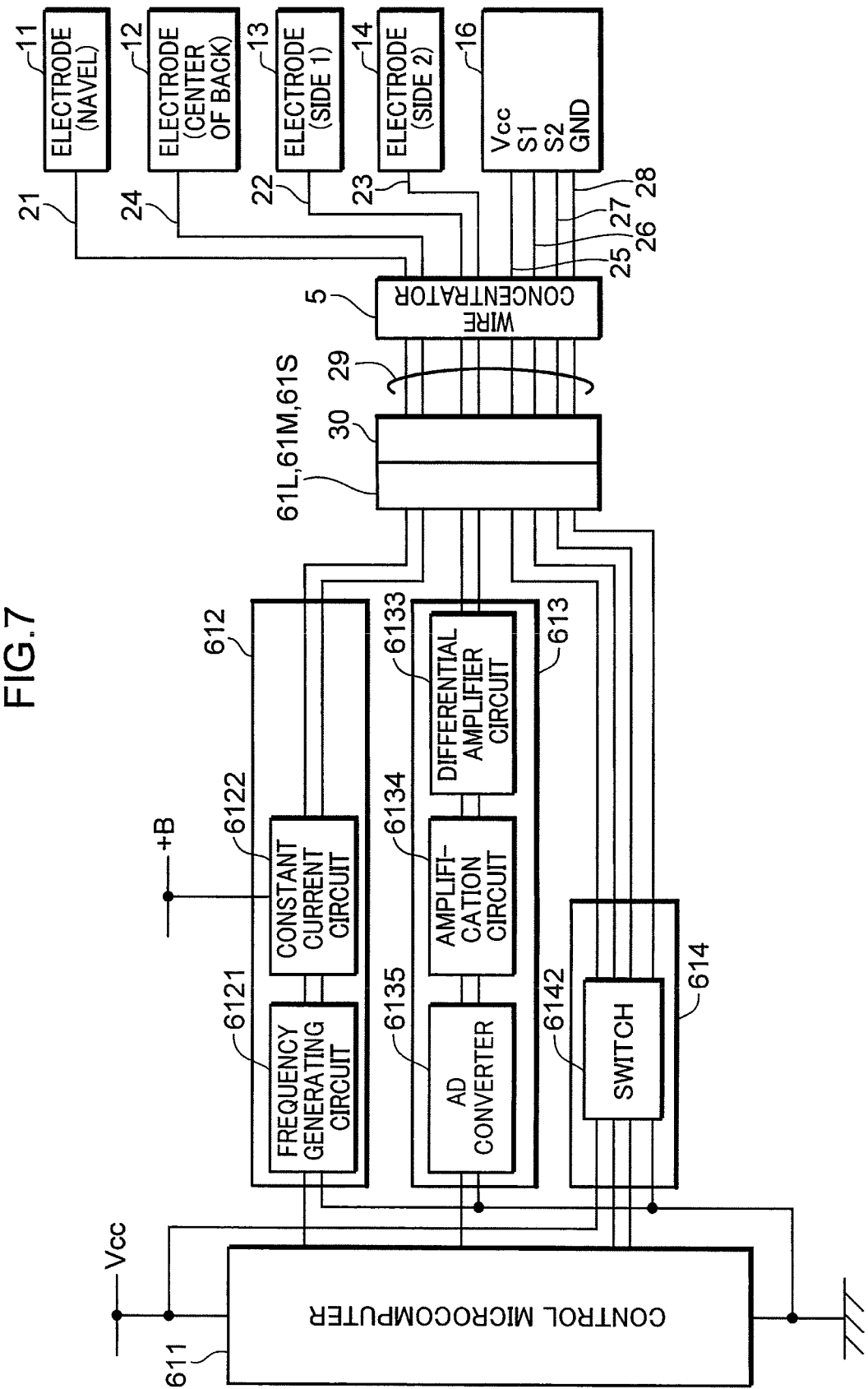
FIG. 7 is a diagram showing a schematic view of the wiring of lead wires in the body fat measurement device shown in FIG. 1.

FIG. 7 shows a schematic view of the relationship between the current application block 612, the voltage measurement block 613, the belt communication block 614, and the lead wires 21 to 28 described above. In FIG. 7, in order to simplify the illustration, the multiplexers 6123, 6124, 6131, 6141, the variable resistors RS1, RS2, RM1, RM2, RL1, RL2, and so on, are not depicted.

The switch 6142 is not limited to an electrical switch which can be controlled to open and close electrically, such as a transistor or other semiconductor element, or a relay switch, or the like, and may also be a mechanical switch which can be operated manually. In the case of an electrical switch, it is possible to shut off the lead wires 25 to 28 automatically without the subject being aware, by controlling the opening and closing of the switch 6142 by the control microcomputer 611. Moreover, if a manual mechanical switch is used as the switch 6142, then it is possible to shut off the lead wires 25 to 28 at low cost.

The measurement unit 16 of the abdominal circumference meter 4 comprises a sensor 162 which performs abdominal circumference measurement, such as reading out magnetic strips or slits as described above, by receiving a supply of power from the main body 6, a control microcomputer 161 which controls the operation of the sensor 162, and a memory for calculation processing (EEPROM) 163. The control microcomputer 161 performs serial communication with the control microcomputer 611 via the lead wires 26, 27. By this means, the abdominal circumference measurement data is output from the control microcomputer 161 to the control microcomputer 611 via the lead wires 26, 27, as a serial communication signal.

Figure 8:
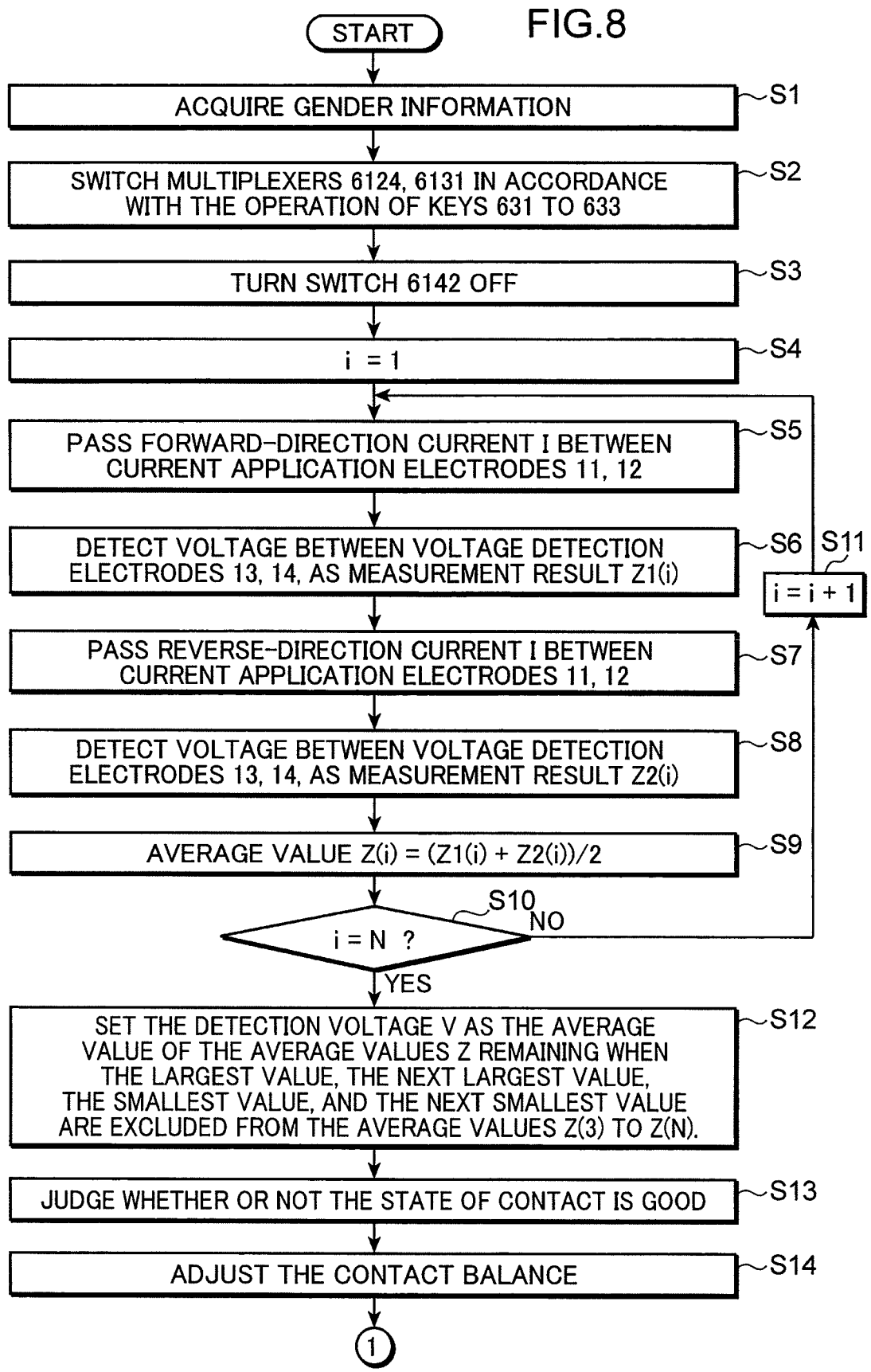
FIG. 8 is a flowchart showing one example of the operation of the body fat measurement device 1 shown in FIG. 1.
Figure 9:
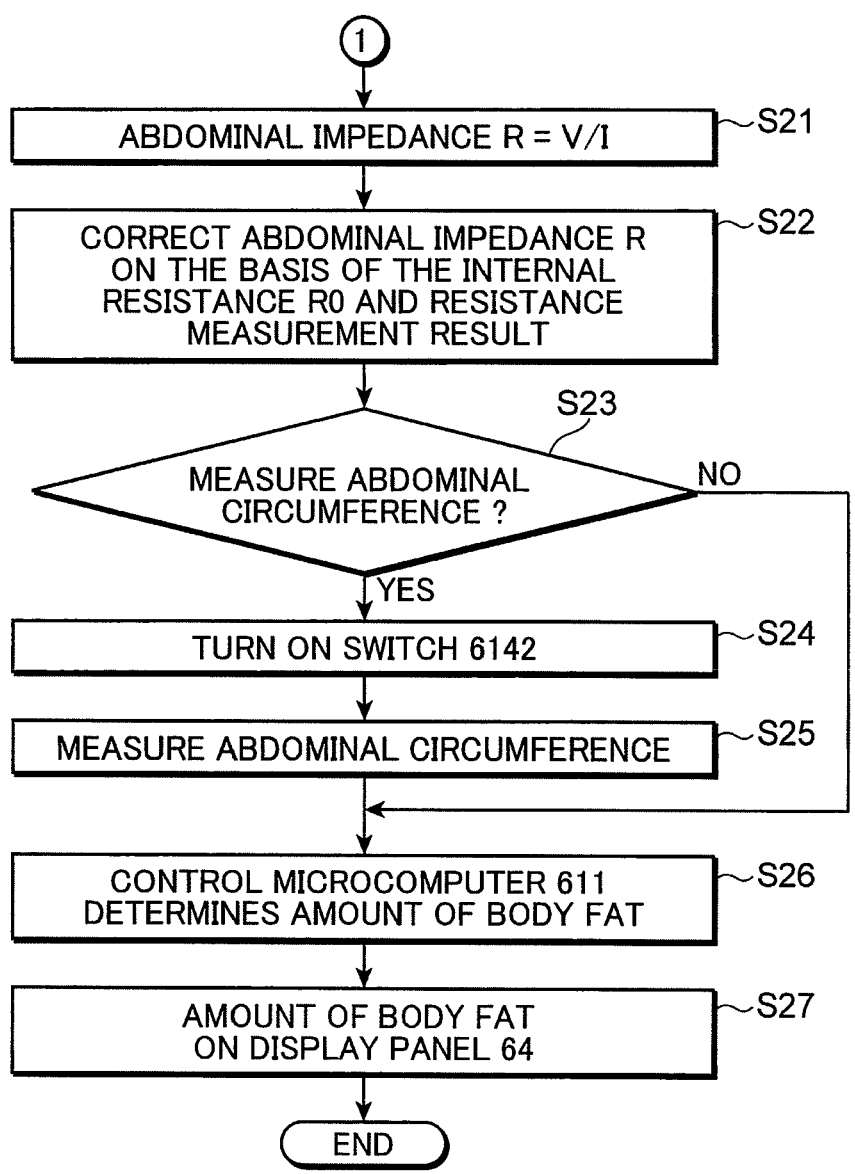
FIG. 9 is a flowchart showing one example of the operation of the body fat measurement device 1 shown in FIG. 1.

Next, the operation of the body fat measurement device 1 which is composed as described above will be explained. FIG. 8 and FIG. 9 are flowcharts showing one example of the operation of the body fat measurement device 1 shown in FIG. 1. In the flowchart described below, the same operations are labeled with the same step numbers and repeated description thereof is omitted. In the body fat measurement device 1 composed as described above, when the power key 621 is operated on the operation control board 62, a power supply is input to the body fat measurement device 1.

When the man or woman selection keys 624, 625 are operated, a man/woman selection is performed, and information indicating the gender of the subject 2 is output to the control microcomputer 611 from the selection keys 624, 625. The corresponding indicator (LED) 629, 630 is lit up by the control microcomputer 611. In this way, information indicating the gender of the subject 2 is acquired by the control microcomputer 611 (step S1).

Furthermore, when the visceral fat measurement key 622 is operated, the control microcomputer 611, which is one example of a calculation unit, lights up the corresponding indicator (LED) 627. The control microcomputer 611 then switches the multiplexers 6124, 6131 to the connector 61S, 61M, 61L corresponding to the belt selected by the keys 631 to 633, in accordance with an algorithm stored in a memory 615 consisting of a non-volatile EEPROM, or the like (step S2).

The control microcomputer 611 drives the current application block 612 and the voltage measurement block 613 as described above, and carries out measurement of the abdominal impedance.

More specifically, the control microcomputer 611 firstly turns the switch 6142 off, in other words, turns off the transistors which constitute the switch 6142 (step S3). By this means, the connection between the lead wires 25 to 28 which are one example of second core wires and the calculation unit is shut off.

Next, 1 is substituted for the variable i by the control microcomputer 611 (step S4). A current I in the forward direction is passed between the current application electrodes 11, 12 by the current application block 612, in accordance with the control signal from the control microcomputer 611 (step S5).

Thereupon, the voltage between the voltage detection electrodes 13, 14 while the forward-direction current I is passing between the current application electrodes 11, 12 is measured as a measurement result $Z1(i)$ by the voltage measurement block 613 (step S6).

Next, a current I is passed in the reverse direction between the current application electrodes 11, 12, by the current application block 612, in accordance with a control signal from the control microcomputer 611 (step S7).

Thereupon, the voltage between the voltage detection electrodes 13, 14 during the passing of the reverse-direction current I between the current application electrodes 11, 12 is measured as the measurement result $Z2(i)$ by the voltage measurement block 613 (step S8).

Here, when the measurement result $Z1(i)$ and the measurement result $Z2(i)$ are measured, the switch 6142 turns off and the connection between the lead wires 25 to 28, which are one example of second core wires, and the control microcomputer 611 is shut off. If it is supposed that the connection between the lead wires 25 to 28 (second core wires) and the control microcomputer 611 is not shut off, then the lead wires 21, 24 (first core wires) which connect the current application block 612 and the current application electrodes 11, 12, and the lead wires 22, 23 (first core wires) which connect the voltage measurement block 613 and the voltage detection electrodes 13, 14 become coupled to the lead wires 25 to 28 due to line-to-line capacitance, as a result of which a circuit is formed which links the power source of the control microcomputer 611 to which the lead wires 25 to 28 are connected, the circuit ground (GND), and the signal line, with the current application block 612 and the voltage measurement block 613, by means of the line-to-line capacitance.

Therefore, noise generated by the control microcomputer 611 is superimposed on the lead wires 21, 24 and the lead wires 22, 23, and there is risk of decline in the measurement accuracy of the measurement result $Z1(i)$ and the measurement result $Z2(i)$.

However, the body fat measurement device 1 shown in FIG. 1 carries out measurement of the measurement result $Z1(i)$ and the measurement result $Z2(i)$ in a state where the switch 6142 is turned off and the connection between the lead wires 25 to 28 and the control microcomputer 611 is shut off, and therefore the noise generated by the control microcomputer 611 is not superimposed on the lead wires 21, 24 and the lead wires 22, 23, and the measurement accuracy of the measurement result $Z1(i)$ and the measurement result $Z2(i)$ is improved.

Thereupon, the control microcomputer 611 calculates an average value $Z(i)$ of the measurement result $Z1(i)$ and the measurement result $Z2(i)$ (step S9). The measurement result $Z1(1)$, the measurement result $Z2(1)$ and the average value $Z(1)$ indicate first measurement values for the measurement result Z1, the measurement result Z2 and the average value Z; the measurement result $Z1(2)$, the measurement result $Z2(2)$ and the average value $Z(2)$ indicate second measurement values for the measurement result Z1, the measurement result Z2 and the average value Z; and the measurement result $Z1(i)$, the measurement result $Z2(i)$ and the average value $Z(i)$ indicate ith measurement values for the measurement result Z1, the measurement result Z2 and the average value Z. Furthermore, if there is no need to specify the number of measurements in particular, then the notation, measurement result Z1, measurement result Z2 and average value Z, is used.

Next, the control microcomputer 611 checks whether or not the variable i has reached a predetermined number of measurements N (step S10). If the variable i has not reached the number of measurements N, then the control microcomputer 611 increments the variable i by 1 (step S11) and transfers again to step S5. On the other hand, if the variable i has reached the number of measurements N, then the control microcomputer 611 transfers to step S12.

Here, in the measurement in steps S5 to S9, the measurement period is set to a period during which measurement can be performed while the subject holds his or her breath, for example, 6 seconds, and the measurement cycle, in other words, the cycle at which the steps S5 to S9 is repeated, is set to 500 msec. The number of measurements N is set to 12 times. The control microcomputer 611 has an internal standby period during the first two measurements in order to stabilize spike noise, and the like, and uses the measurement results obtained in the remaining ten measurements. The first two measurements may not be executed in steps S6 and S7. In one measurement, the control microcomputer 611 drives the multiplexer 6123, successively performs two times of measurement by switching the current application direction, and sets the average value of the respective average values in the forward and reverse directions as the measurement value. Of the ten average value data thus obtained, the two largest values and the two smallest values are excluded, and the remaining six average values are used as the detection voltage V for calculating the abdominal impedance.

More specifically, the control microcomputer 611 defines the detection voltage V as the average of the six average values Z remaining after the largest value, the next largest value, the smallest value and the next smallest value have been removed from the average values Z(3) to Z(12) (step S12).

Thereupon, the control microcomputer 611 judges whether or not the state of contact of the current application electrodes 11, 12 and the voltage detection electrodes 13, 14 on the surface of the subject 2 is good (step S13), and adjusts the contact balance in accordance with requirements (step S14). The judgment regarding the state of contact (step S13) and the adjustment of the contact balance (step S14) are described hereinafter.

Next, the control microcomputer 611 calculates the abdominal impedance R by using Formula (1) given above (step S21).

Thereupon, the control microcomputer 611 corrects the abdominal impedance R on the basis of the resistance value measurement results of the internal resistance R0 (step S22). More specifically, the control microcomputer 611 switches the multiplexers 6124, 6131 to the internal resistance R0 side of the dummy, supplies the current I to the internal resistance R0 by means of the current application block 612, and measures the voltage between the respective ends of the internal resistance R0, as the detection voltage V, by means of the voltage application block 613. The control microcomputer 611 measures the resistance value of the internal resistance R0, by dividing the detection voltage V obtained in this way, by the current I, to calculate the resistance value of the internal resistance R0.

The resistance value of the internal resistance R0 is set previously to 1Ω, for example, as a reference. The resistance value of the internal resistance R0 is measured within one second, for instance, and of the measurement values obtained in two measurements at an interval of 500 msec apart as described above, the first data is discarded in order to remove spike noise, and the like, and the second data is used as the internal resistance value.

The resistance value of the internal resistance R0 changes with temperature. The control microcomputer 611 then compares the resistance value of the internal resistance R0 measured in this way with a measurement value upon shipment, which is stored in the memory 615, and the differential value dR therebetween is calculated. A look-up table showing associations between the amount of change of the abdominal impedance R with respect to the temperature and the differential value dR is determined previously by experimentation and stored in the memory 615. The control microcomputer 611 refers to the look-up table in order to acquire the amount of change stored in association with the differential value dR, as a correction value, and corrects the abdominal impedance R by adding or subtracting this correction value to or from the abdominal impedance R calculated at step S21. By this means, the variation in the measurement value with temperature is corrected and the measurement accuracy of the abdominal impedance R is improved.

If the abdominal circumference measurement key 623 is not operated when the visceral fat measurement key 622 is operated (NO at step S23), then the control microcomputer 611 transfers to step S26 without carrying out abdominal circumference measurement.

On the other hand, if the abdominal circumference measurement key 623 is operated (YES at step S23), then after the measurement of the abdominal impedance R described above, the control microcomputer 611 switches the multiplexer 6141 to the connector corresponding to the selected belt, of the connectors 61S, 61M, 61L. The switch 6142 is then turned on, in other words, the respective transistors constituting the switch 6142 are turned on (step S24).

The control microcomputer 611 communicates with the control microcomputer 161 of the measurement unit 16, causes the measurement unit 16 to measure the abdominal circumference, and receives data indicating the measurement result for the abdominal circumference from the measurement unit 16 (step S25).

Thereupon, when gender information due to the selection of the man/woman selection keys 624, 625 has been acquired, when data about the height and weight of the subject 2 has been input from the personal computer 7, and when a abdominal circumference measurement result has been obtained, then the control microcomputer 611 uses this respective data to refer to the look-up table stored in the memory 615 and acquire an amount of body fat associated with these parameters (step S26).

The calculation result for the amount of body fat thus obtained is displayed on the display panel 64 by the control microcomputer 611, and is also sent to the personal computer 7 (step S27). During this measurement, an error judgment operation such as that described in detail hereinafter is also carried out, and if there is not judged to be an error, then the measurement value is taken to be valid.

Figure 10:
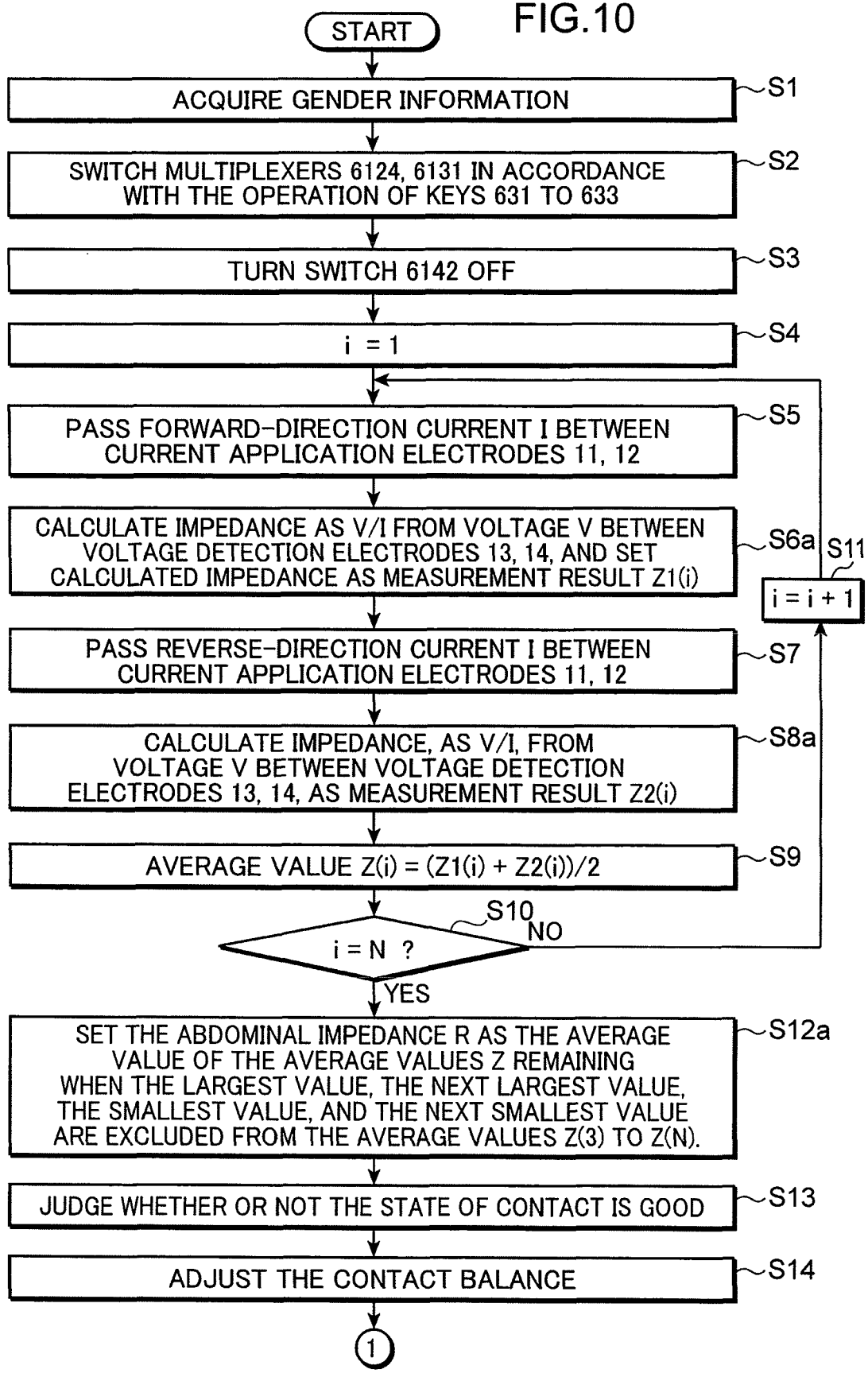
FIG. 10 is a flowchart showing one example of the operation of the body fat measurement device 1 shown in FIG. 1.

As shown in FIG. 10, in step S6a, the voltage V between the voltage detection electrodes 13, 14 during the passage of the forward-direction current I between the current application electrodes 11, 12 is measured by the voltage measurement block 613, and the control microcomputer 611 may calculate a first abdominal impedance by V/I, from the voltage V obtained in this way, and may set the first abdominal impedance calculated in this way as the measurement result Z1(i).

Furthermore, in step S8a, the voltage V between the voltage detection electrodes 13, 14 during the passage of the reverse-direction current I between the current application electrodes 11, 12 is measured by the voltage measurement block 613, and the control microcomputer 611 may calculate a second abdominal impedance by V/I from the voltage V obtained in this way and may set the second abdominal impedance calculated in this way as the measurement result Z2(i).

A composition may be adopted in which, at step S12a, the control microcomputer 611 takes the abdominal impedance R to be the average value of the six average values Z which remain when the largest value, the next largest value, the smallest value and the next smallest value are excluded from the average values Z(3) to Z(12), and does not execute step S21.

In this way, the measurement results Z1, Z2 and the average value Z may be voltage values as shown in FIG. 8, or may be impedance values as shown in FIG. 10.

Furthermore, an example is described in which, in steps S5 to S11, the measurement results Z1, Z2 and the average value Z are obtained a plurality of times, but it is also possible to acquire the measurement results Z1, Z2 and the average value Z one time and to set this average value Z directly as the detection voltage V.

Moreover, in steps S12, S12a, the average value of the average values Z(1) to Z(N) may be set as the detection voltage V or the abdominal impedance R.

Furthermore, an example is described in which the detection voltage V and the abdominal impedance R are determined by using an average value Z of measurement values Z1, Z2, but it is also possible to determine only one of the measurement results Z1, Z2, and to use this measurement result as the detection voltage V and the abdominal impedance R.

It should be noted that in the body fat measurement device 1, the control microcomputer 611 turns off the switch 6142 when measuring the abdominal impedance as described above by using the current application block 612 and the voltage measurement block 613, thereby isolating the lead wires 25 to 28 for the measurement unit 16 which performs abdominal circumference from the main body 6. If a size connector 30 is not installed, then the function of an isolating unit is achieved by switching the multiplexer 6141 to a connector other than the connector of the belt which is the measurement object, and the switch 6142 can be omitted. In this case, the multiplexer 6141 is one example of an isolating unit.

By adopting this composition, in a body fat measurement device 1 of a belt type which calculates an amount of body fat by taking account of other parameters, desirably, gender, weight, abdominal circumference, and the like, in relation to the abdominal impedance of the subject, it is possible to measure the abdominal circumference as described above, which is another parameter that is different to the abdominal impedance and that can assist the calculation of the amount of body fat, with the belt 3. In providing the measurement unit 16 as a second measurement unit which performs measurement of the abdominal circumference, even if, for the purpose of usability, costs, and the like, a cable 29 is used in which the lead wires 21, 24; 22, 23 which are first core wires that respectively connect the current application block 612 and the voltage measurement block 613, which is a first measurement unit, with the corresponding pairs of electrodes 11, 12; 13, 14, and the lead wires 25 to 28 which are second core wires that connect the control microcomputer 161 of the measurement unit 16 with the control microcomputer 611 to which the corresponding measurement results are input, are provided inside the same insulating coating (are formed an integrated fashion), a switch 6142 is provided between the lead wires 25 to 28 and the control microcomputer 611, and the line-to-line capacitance of the lead wires 25 to 28 is isolated by means of the switch 6142 during measurement of the abdominal impedance.

Consequently, if a further second measurement unit which is capable of measuring a different parameter other than the abdominal impedance, that can assist in the calculation of the amount of body fat, is provided on the same belt 3, it is also possible to suppress decline in the measurement accuracy of the abdominal impedance, in other words, the measurement accuracy of a very small voltage.

On the other hand, the measurement of the abdominal circumference by the measurement unit 16 which forms a second measurement unit can be completed on the belt 3 side, in other words, can be carried out via the lead wires 25 to 28 without involving the main body 6. However, if the measurement by the second measurement unit is affected by the line-to-line capacitance of the lead wires 21, 24; 22, 23 which connect the current application block 612 and the voltage measurement block 613 for measuring abdominal impedance with the corresponding electrodes 11, 12; 13, 14, then an isolating unit should be provided in similar fashion in order to shut off the current application block 612 and the voltage measurement block 613 from the electrodes 11, 12; 13, 14.

Moreover, the measurement unit 16 which is the second measurement unit is able to measure the abdominal circumference, which is very important in the calculation of an accurate amount of body fat, easily just by fitting the belt 3, through measuring the length of the belt 3 that is in contact with the surface 2b of the subject, this length corresponding to the abdominal circumference.

Furthermore, of the electrodes 11, 12; 13, 14, the pair of electrodes 11, 12 which apply current, are situated at the center of the abdomen (navel) 2c of the subject 2, and at the center of the back (spine) 2d of the subject, and consist of metal electrodes which are pressed against the surface 2b of the subject 2 by the belt 3, whereas the other electrodes 13, 14 which detect a very weak voltage are gel electrodes which are stuck at front and rear positions of the side 2e of the subject 2, through the opening 32a formed in the belt 3, and the positions of this other pair of electrodes 13, 14 can easily be adjusted finely, variations due to difference in the pressing force are eliminated, and uniform measurement conditions can be maintained easily for each measurement operation.

Furthermore, in the current application block 612, the direction in which the current flows is switched by the multiplexer 6123, a current is passed between the pair of electrodes 11, 12 from the navel side to the back, and in reverse, from the back to the navel side, and the control microcomputer 611 determines the abdominal impedance from the average value of the two measurement results produced by the voltage measurement block 613, thus making it possible to improve the measurement accuracy of the abdominal impedance and consequently also raising the measurement accuracy of the amount of body fat.

Next, the judgment of whether or not the state of contact is good in step S13 will be described. The control microcomputer 611 functions as a contact judgment unit which judges fluctuation in the contact resistance between the electrodes 11 to 14 and the surface 2b of the subject 2, in other words, whether or not the electrodes 11 to 14 are in good contact with the surface 2b of the subject 2, from the measurement results of the measurement of the abdominal impedance described above, by executing a control program which is stored in the memory 615.

A buzzer 616 is installed as a warning generation unit on the main board 61, and if an abnormality is judged, the control microcomputer 611 sounds the buzzer 616 and also displays an error mode (the conditions relating to the abnormality) on the display panel 64. Furthermore, the error mode may also be displayed on the personal computer 7. Below, the details of each of a plurality of error modes are described in detail.

The control microcomputer 611 which serves as a contact judgment unit functions as the first to fifth judgment unit.

Firstly, the control microcomputer 611 forming the first judgment unit judges an error mode 1 as described below. More specifically, the control microcomputer 611 infers the state of the contact resistance between the voltage detection electrodes 13, 14 and the surface 2b of the subject from the average value Z of the two measurement results Z1, Z2 produced by the voltage measurement block 613 in response to the application of current in the forward direction and reverse direction by the current application block 612.

If the average value Z is considerably smaller than a predetermined first threshold value TH1, then it is judged that the voltage detection electrodes 13, 14 are floating, in other words, that a defect has occurred in the contact between the two voltage detection electrodes 13, 14 and the surface 2b.

If the voltage value is used as the average value Z, then the threshold value TH1 is 2.7 V, for instance, and if the abdominal impedance is used as the average value Z, then the threshold value TH1 is 0.4Ω, for instance. Taking the application of current in the forward and reverse directions as one measurement, then if the conditions of the error mode 1 are satisfied at least once in the average values Z(3) to Z(12) of the ten measurements as described above, the control microcomputer 611 judges that a defect has occurred in the contact between the voltage detection electrodes 13, 14 and the body surface 2b.

Figure 11:
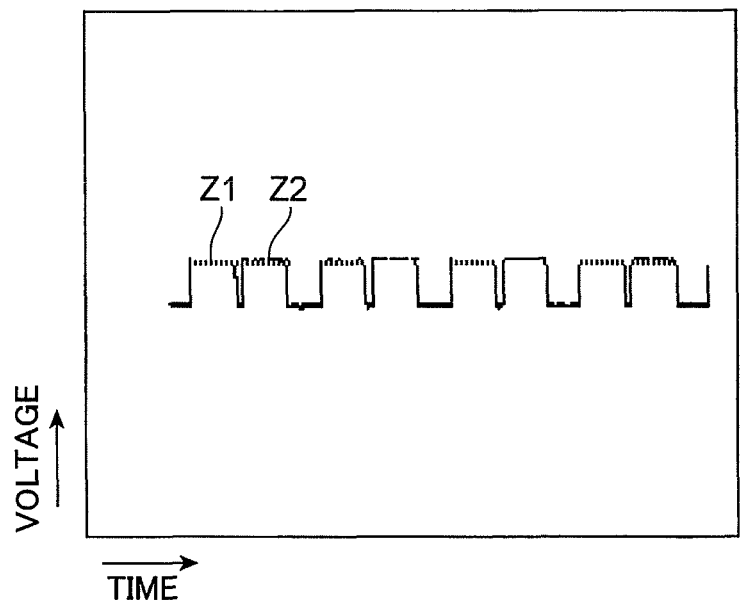
FIG. 11 is a waveform diagram for describing a method of judging an electrode contact defect (in a normal situation).
Figure 12:
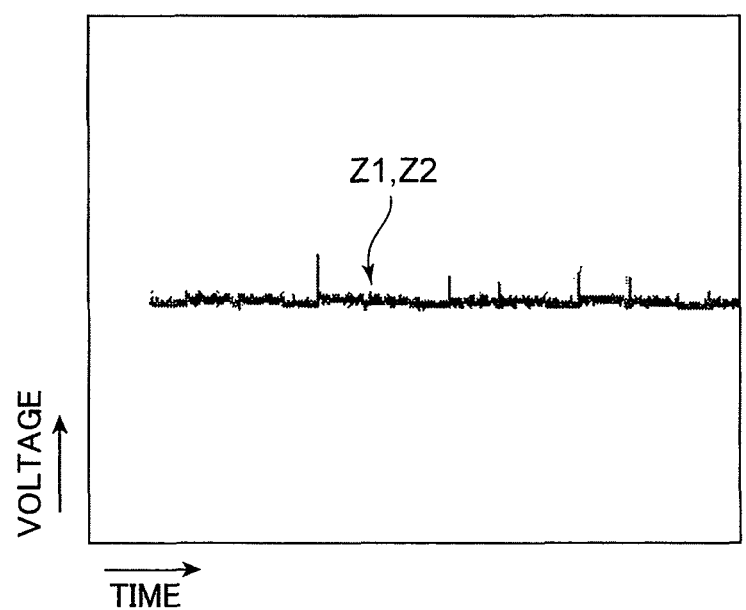
FIG. 12 is a waveform diagram for describing a method of judging an electrode contact defect (error mode 1).

By this means, it is possible to provide an appropriate response in cases where, for instance, the voltage detection electrodes 13, 14 are detached. FIG. 12 shows a detection voltage waveform produced by the voltage measurement block 613 when floating occurs between the voltage detection electrodes 13, 14, and FIG. 11 shows the detection voltage waveform when all of the electrodes 11 to 14 are installed correctly. As is clear from FIG. 12, when floating has occurred in the two voltage detection electrodes 13, 14, the two measurement results Z1, Z2 appear as the noise floor.

Next, the control microcomputer 611 forming the second judgment unit carries out judgment of error mode 2 as described below. More specifically, if the average value Z obtained from the average value Z of the two measurement results Z1, Z2 is considerably larger than a predetermined second threshold value TH2, then the control microcomputer 611 judges that a defect in the contact with the body surface 2b has occurred in either one of the voltage detection electrodes 13, 14, for instance, that one of the voltage detection electrodes 13, 14 is not making adequate contact or has become disconnected, or that the skin has become dry.

The threshold value TH2 is 4.5 V, for instance, when the voltage value is used as the average value Z, and is 4.3Ω, for instance, when the abdominal impedance is used as the average value Z. If the condition of error mode 2 is satisfied at least once in the ten average values Z(3) to Z(12), then the control microcomputer 611 judges that a defect has occurred in the contact with the body surface 2b in either one of the voltage detection electrodes 13, 14.

Figure 13:
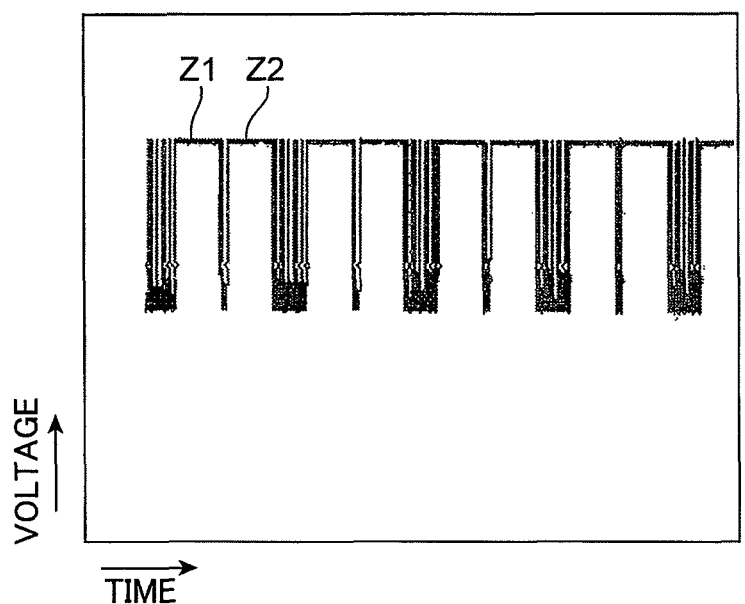
FIG. 13 is a waveform diagram for describing a method of judging an electrode contact defect (error mode 2).

By this means, it is possible to judge that one of the voltage detection electrodes 13, 14 is detached. FIG. 13 shows a detection voltage waveform produced by the voltage measurement block 613 in a state where one of the voltage detection electrodes 13, 14 is not making adequate contact. As FIG. 13 reveals, if one of the voltage detection electrodes 13, 14 is not making adequate contact, then the two measurement results Z1, Z2 both become extremely large.

Moreover, the control microcomputer 611 forming the third judgment unit (or a third determiner) carries out judgment of the error mode 3 as described below. The control microcomputer 611 judges that a defect has occurred in the contact with the body surface 2b in one of the current application electrodes 11, 12, if one of the two measurement results Z1(i) and Z2(i) is smaller than a first threshold value TH1' and the other measurement result is greater than a second threshold value TH2'. In this case, if the condition of error mode 3 is satisfied in any set of measurement results Z1(i), Z2(i) in the range of i=3 to N, then it is judged that a defect has occurred in the contact with the body surface 2b in one of the current application electrodes 11, 12.

More specifically, in a state where the current application electrode 11 (one electrode) is in contact with the center of the subject's abdomen (navel) 2c and the current application electrode 12 (other electrode) is in contact with center of the subject's back (spine) 2d, the control microcomputer 611 obtains a measurement result Z1 by applying a constant current pulse to the multiplexer 6123 which sets the current application electrode 11 on the abdomen center (navel) 2c side to a high level, in the first of the two measurements.

Thereupon, the control microcomputer 611 obtains a measurement result Z2 by applying a constant current pulse which sets the current application electrode 12 on the back center (spine) 2d side to a high level.

Thereupon, if Z1<TH1' and Z2>TH2', then the control microcomputer 611 judges that the current application electrode 11 on the abdomen center (navel) 2c side is not making adequate contact (error mode 3-1), and if Z1>TH2' and Z2<TH1', then the control microcomputer 611 judges that the current application voltage 12 on the back center (spine) 2d side is not making adequate contact (error mode 3-2).

Figure 14:
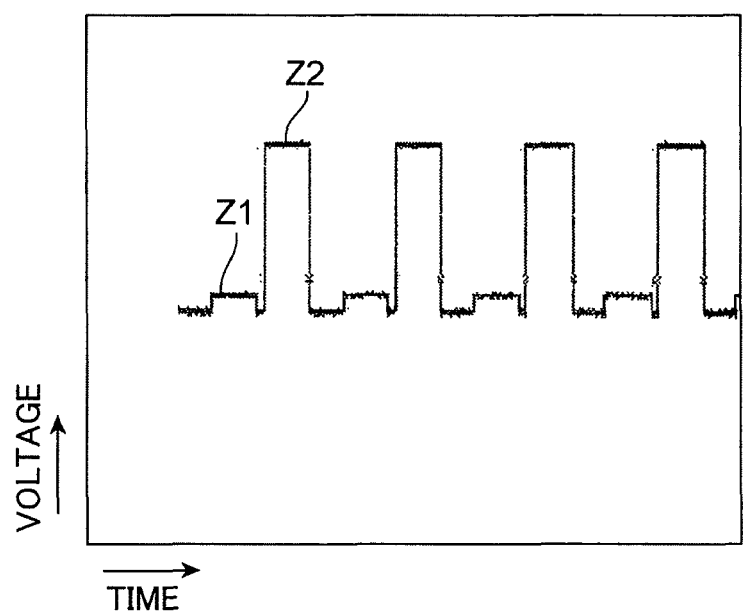
FIG. 14 is a waveform diagram for describing a method of judging an electrode contact defect (error mode 3-1).
Figure 15:
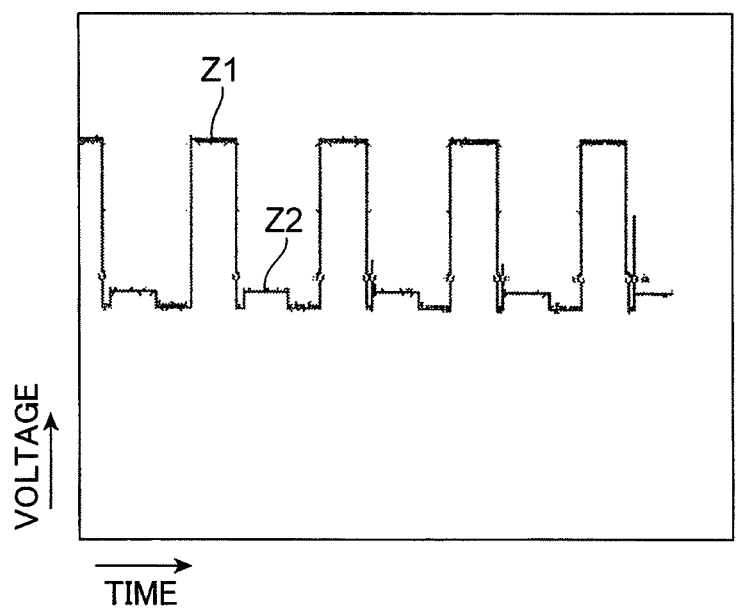
FIG. 15 is a waveform diagram for describing a method of judging an electrode contact defect (error mode 3-2).

The first judgment value TH1' and the second judgment value TH2' are respectively 3.0 V and 4.5 V, for instance, when the voltage value is used for the measurement results Z1, Z2, and are respectively 1.1Ω and 4.3Ω, for instance when the impedance is used for the measurement results Z1, Z2. By this means, it is possible to judge detachment of the current application electrodes 11, 12. The detection voltage waveform produced by the voltage measurement block 613 in this case is shown in FIG. 14 (error mode 3-1) and FIG. 15 (error mode 3-2). As FIG. 14 and FIG. 15 clearly reveal, if the current application electrodes 11, 12 do not make adequate contact, then a very large differential appears between the two measurement results Z1, Z2.

Furthermore, the control microcomputer 611 forming the fourth judgment unit (or a fourth determiner) carries out judgment of an error mode 4, as described below. The control microcomputer 611 judges the contact balance between the voltage detection electrodes 13, 14 from the differential |Z1 −Z2| between the two measurement results Z1, Z2. More specifically, if the differential |Z1 −Z2| is larger than a predetermined third threshold value TH3, then the contact balance between the voltage detection electrodes 13, 14 is judged to be poor.

The threshold value TH3 is 0.5 V, for example, when the voltage value is used for the measurement results Z1, Z3, and is 1.1Ω, for example, when the impedance is used for the measurement results Z1, Z2. The control microcomputer 611 judges that the contact balance between the voltage detection electrodes 13, 14 is poor, among the ten measurement results Z1(3) to (12) and Z2(3) to (12).

Figure 16:
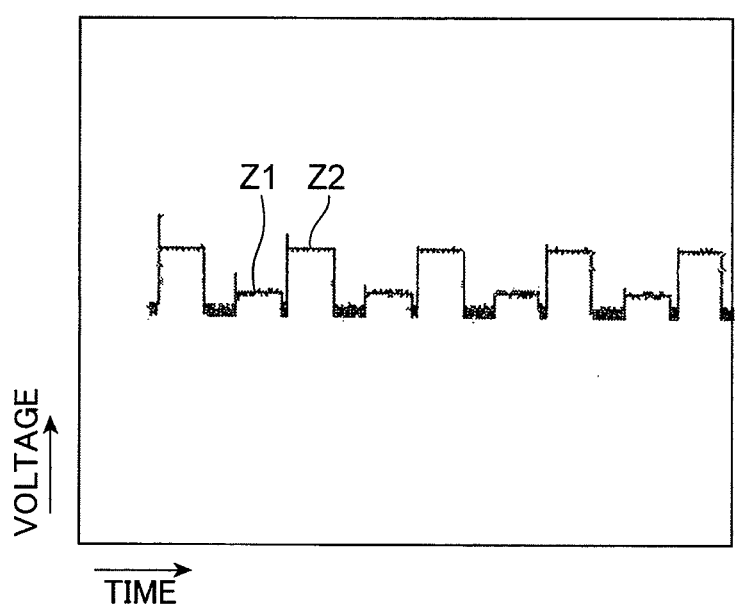
FIG. 16 is a waveform diagram for describing a method of judging an electrode contact defect (error mode 4).

By this means, it is possible to judge that the balance of contact between the voltage detection electrodes 13, 14 and the body surface 2b is poor, for example, that one of the electrodes is detached. FIG. 16 shows a detection voltage waveform produced by a voltage measurement block 613 in this case. As FIG. 16 reveals, if the contact balance of the voltage detection electrodes 13, 14 is poor, then a difference occurs between the two measurement results Z1, Z2.

Moreover, the control microcomputer 611 which forms a fifth judgment unit (or a fifth determiner) carries out judgment of an error mode 5 as described below. Taking one sample to be the average value Z of two measurement results Z1, Z2, of the ten samples obtained, the two largest values and the two smallest values are excluded in steps S12, S12a, to leave six samples, and if the maximum and minimum values of these six samples are greatly disparate and the difference therebetween is greater than a predetermined fourth threshold value TH4, then the control microcomputer 611 judges that the data has been disrupted due to irregular breathing or body movements, or the like. If an impedance is used for the measurement results Z1, Z2, then the fourth threshold value TH4 is 0.2 Ω, for example.

The judgment methods of the respective error modes described above are summarized in Table 1 below.

TABLE 1

| Error Mode | Judgment | Cause | Threshold value Voltage (V) | Threshold value Z (Ω) |
|---|---|---|---|---|
| 1 | Z < TH1 (at least once) | Both side electrodes are floating | 2.7 | 0.4 |
| 2 | Z > TH2 (at least once) | One of the side electrodes is not making adequate contact. The wire is disconnected or the skin is dry. | 4.5 | 4.3 |
| 3-1 | Z1 < TH1' and Z2 > TH2' (at least once) | The navel electrode is not making adequate contact. | TH1' = 3.0 | TH1' = 1.1 |
| 3-2 | Z1 > TH2' and Z2 < TH1' (at least once) | The back electrode is not making adequate contact. | TH2' = 4.5 | TH2' = 4.3 |
| 4 | |Z1 − Z2| > TH3 (no less than 5 times in ten) | The balance between the front/rear side electrodes is poor. | Δ0.5 | Δ1.1 |
| 5 | Difference between maximum and minimum values of six Z data is greater than TH4 | Breathing is irregular or data is instable due to body movement. | — | 0.2 |

As described above, at step S13, the control microcomputer 611 judges the state of contact between the electrodes 11 to 14 and the body surface 2b of the subject 2, and if the contact is defective, issues a warning to the user by, for instance, displaying the judgment result on the display panel 64. In this way, the defective contact of the electrodes is reported to the user, such as the subject or inspection technician, and a repeated measurement operation is prompted, thereby making it possible to achieve accurate measurement reliably by causing the user to adjust the belt 3 and the electrodes 11 to 14.

Furthermore, at step S14, if the visceral fat measurement key 622 is operated again while a defective contact is being reported, then the control microcomputer 611 is able to limit the extent of the decline in measurement accuracy by adjusting the variable resistors RS2, RM2, RL2 in the voltage measurement block 613 so as to change the impedance of the current path passing through the voltage detection electrodes 13, 14 in line with the magnitude of the previously detected contact resistance, if the contact of the current application electrodes 11, 12 is poor (error mode 3-1, 3-2) or if the contact balance between the voltage detection electrodes 13, 14 is poor (error mode 4).

Furthermore, if the contact of one of the voltage detection electrodes 13, 14 is poor (error mode 2), then the control microcomputer 611 is able to limit the extent of decline in the measurement accuracy by adjusting the resistance values of the variable resistors RS1, RM1, RL1 in the current application block 612 so as to change the impedance of the current path passing through the current application electrodes 11, 12.

If the contact of the electrodes 11 to 14 is inadequate, as in error modes 2, 3-1, 3-2, 4, then fluctuation can be compensated for by means of the variable resistors RS1, RM1, RL1; RS2, RM2, RL2, and in the case of a detached electrode (error mode 1), while the control microcomputer 611 continues to issue a warning, it is reported via the display panel 64 or the personal computer 7 that compensation for the fluctuation is not possible. Moreover, in the case of a measurement failure (error mode 5), it is possible to carry out measurement again, without readjustments.

By adopting a composition of this kind, it is possible to correct the contact resistance and suppress fluctuations by adjusting the variable resistors RS1, RM1, RL1; RS2, RM2, RL2, if there is a problem with the contact resistance. By this means, it is possible to reduce the extent of decline in the measurement accuracy, without refitting the electrodes to the subject.

(Second embodiment)

Figure 17:
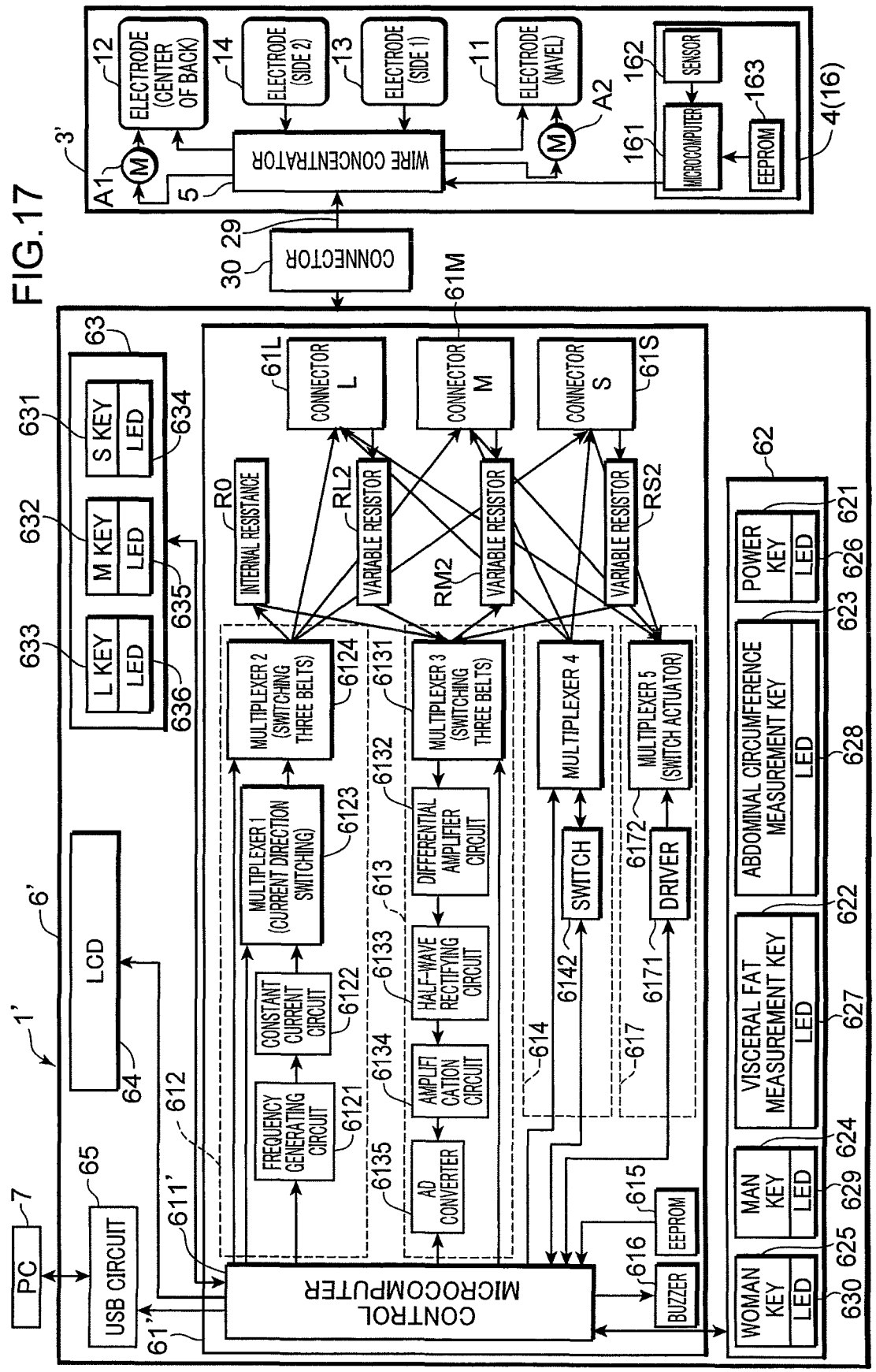
FIG. 17 is a block diagram showing the electrical composition of a belt-type body fat measurement device relating to a further embodiment of the present invention disclosure.

FIG. 17 is a block diagram showing the electrical composition of a belt-type body fat measurement device 1' relating to a further embodiment of the present disclosure.

This body fat measurement device 1' is similar to the body fat measurement device 1 shown in FIG. 6, and corresponding parts are labeled with the same reference numerals and description thereof is omitted here. The point to be noted is that in the body fat measurement device 1', an actuator drive block 617 is provided instead of the variable resistors RS1, RM1, RL1 corresponding to the current application block 612 described above, in the main board 61' of the main body 6'. In accordance with this, in the belt 3', actuators A1, A2 are provided on the current application electrodes 11, 12.

The actuators A1, A2 are constituted by motors and drive mechanisms which push the current application electrodes 11, 12 embedded respectively in the buckle 31 and the abdominal circumference meter 4 outwards toward the subject 2. Alternatively, if the voltage detection electrodes 13, 14 are made from movable metal electrodes on the belt 3, then the actuators A1, A2 may also be provided on the voltage detection electrodes 13, 14. On the other hand, the actuator drive block 617 comprises a multiplexer 6172 which switches the size of the belt 3', in a drive circuit 6171 which drives the motor in response to the drive signal from the control microcomputer 611'.

The control microcomputer 611' carries out judgment of error modes 3-1, 3-2 at step S13, and if it is judged that a contact defect has occurred between either of the current application electrodes 11, 12 and the body surface 2b, then at step S14, the actuator on the current application electrode side where a contact defect is judged to have occurred, of the actuators A1, A2, is driven so as to adjust the state of contact of the current application electrode. In this way, the contact between the current application electrodes 11, 12 and the body surface 2b is adjusted, and the fluctuation can be suppressed and the state of contact can be improved. The control microcomputer 611' corresponds to one example of the drive unit.

The body fat measurement devices 1, 1' are described with respect to examples in which belts 3 of a plurality of sizes S, M, L can be switched and connected, but it is not particularly necessary to adopt a composition in which belts 3 of a plurality of sizes can be switched. If there is one type of belt 3, then the multiplexers 2, 3, 4, 5 for belt switching are not necessary.

The body fat measurement device according to one aspect of the present disclosure includes: a belt configured to be wrapped around an abdomen of a subject; a plurality of electrodes which are provided on the belt and configured to contact the body surface of the subject; a current application unit (or a current applier) which passes a predetermined current between a pair of electrodes of the plurality of electrodes; a first measurement unit (or a first measurer) which measures a voltage between another pair of electrodes, of the plurality of electrodes, while the current is passed between the pair of electrodes by the current application unit; a calculation unit which calculates an abdominal impedance of the subject on the basis of the voltage measured by the first measurement unit and calculates an amount of body fat of the subject by using the calculated abdominal impedance; a second measurement unit (or a second measurer) which acquires a parameter other than the abdominal impedance and outputs a signal indicating the measured parameter to the calculation unit (or a calculator); a cable in which a first core wire which connects between at least one of the current application unit and the pair of electrodes, and the first measurement unit and the other pair of electrodes, and a second core wire which connects the second measurement unit and the calculation unit are provided inside the same insulating coating; and an isolating unit which can shut off the connection between the second core wire and the calculation unit, wherein the calculation unit shuts off the connection between the second core wire and the calculation unit by the isolating unit (or an isolator), during measurement of the abdominal impedance, acquires the voltage measured by the first measurement unit while the connection is shut off, and calculates the abdominal impedance on the basis of the acquired voltage.

According to the composition described above, the body fat measurement device of a belt type comprises: a belt which is wrapped around the abdomen of a subject; a plurality of electrodes which are provided on the belt and contact the body surface of the subject; a current application unit which passes a predetermined current, for example, a high-frequency pulse current, between a pair of electrodes of the plurality of electrodes, for example, at the center of the abdomen (navel) of the subject and the center of the back (spine) of the subject; a first measurement unit which measures the voltage between another pair of electrodes, of the plurality of electrodes, for example, electrodes provided at the front and rear of a side (flank) of the subject, while a current is passed between the pair of electrodes by the current application unit; and a calculation unit which calculates an abdominal impedance of the subject on the basis of the voltage measured by the first measurement unit, desirably by taking account of other parameters, such as gender, weight, abdominal circumference, and the like, and calculates an amount of body fat of the subject by using the calculation abdominal impedance.

A second measurement unit which acquires a parameter other than the abdominal impedance and outputs a signal indicating the measured parameter to the calculation unit is provided on the belt, for example. In this, for the purpose of usability, costs, and the like, a cable is used, in which first core wires which connect between at least one of the current application unit and the pair of electrodes, and the first measurement unit and the other pair of electrodes, and second core wires which connect the second measurement unit and the calculation unit, are formed in an integrated fashion, for example, inside the same insulating coating. An isolating unit which can shut off the connection between the second core wires and the calculation unit is provided and the connection between the second core wires and the calculation unit is shut off by the isolating unit so as to eliminate the line-to-line capacitance of the second core wires, during the measurement of the abdominal impedance.

Consequently, if a second measurement unit capable of measuring a parameter other than the abdominal impedance is provided on the same belt, it is possible to reduce the risk of decline in the measurement accuracy of the abdominal impedance, in other words, the measurement accuracy of a very small voltage, due to the line-to-line capacitance of the second core wires. On the other hand, if there are effects due to the line-to-line capacitance of the first core wires which connect the current application unit for measuring the abdominal impedance with the electrodes corresponding to the first measurement unit during the measurement by the second measurement unit, then in a similar fashion, an isolating unit which shuts off the connection between the current application unit and the first measurement unit and the electrodes should be provided.

Furthermore, desirably, the second measurement unit measures the abdominal circumference of the subject as the parameter.

According to the composition described above, the abdominal circumference which is a very useful parameter in improving the calculation accuracy of the amount of body fat, in other words, the length of the belt which is in contact with the body surface of the subject, can easily be measured by the second measurement unit, simply by fitting the belt.

Furthermore, desirably, the pair of electrodes are metal electrodes configured to be provided in a center of the abdomen (navel) and a center of the back (spine) of the subject, and the another pair of electrodes are gel electrodes which are configured to be attached to the front and rear sides of the subject.

According to the composition described above, the pair of electrodes which perform the current application are provided on the center of the abdomen (navel) and the center of the back (spine) of the subject, and are constituted by metal electrodes which are pressed against the body surface of the subject by the belt, whereas the pair of other electrodes which detect a very weak voltage are gel electrodes which are attached to the front and rear of a side of the subject.

Consequently, fine adjustment of the positions of the other pair of electrodes can be carried out easily, and furthermore non-uniformities due to differences in the pressing force are eliminated and the measurement conditions are kept uniform on each occasion.

The pair of electrodes may be metal electrodes configured to be provided in a center of the abdomen and the center of the back of the subject, and the another pair of electrodes may be metal electrodes which are configured to be attached to the front and rear sides of the subject.

Furthermore, desirably, the current application unit successively passes a current in a forward direction and a current in a reverse direction, the forward direction and the reverse direction being mutually opposite directions as the direction of a current passed between the pair of electrodes is successively switched; and the calculation unit calculates the abdominal impedance on the basis of an average value of respective measurement results of voltages measured by the first measurement unit which correspond respectively to the forward-direction current and the reverse-direction current while the connection is shut off.

According to the composition described above, the current application unit passes a current successively from the navel side to the back and, in reverse, from the back to the navel side, for instance, the first measurement unit carries out voltage measurement during the plurality of passages of current, and the calculation unit determines the abdominal impedance from the average value of the plurality of measurement results.

By this means, it is possible to raise the measurement accuracy of the abdominal impedance, and consequently the measurement accuracy of the amount of body fat can be raised.

Furthermore, the current application unit may successively pass a current in a forward direction and a current in a reverse direction, the forward direction and the reverse direction being mutually opposite directions as the direction of a current passed between the pair of electrodes is successively switched; and the calculation unit may calculate a first abdominal impedance as an impedance measurement result corresponding to the forward-direction current, on the basis of the voltage measured by the first measurement unit which corresponds to the forward-direction current while the connection is shut off, calculate a second abdominal impedance as an impedance measurement result corresponding to the reverse-direction current, on the basis of the voltage measured by the first measurement unit which corresponds to the reverse-direction current while the connection is shut off, and calculate the abdominal impedance on the basis of an average value of the first abdominal impedance and the second abdominal impedance.

By this means, it is possible to raise the measurement accuracy of the abdominal impedance, and consequently the measurement accuracy of the amount of body fat can be raised.

Desirably, the body fat measurement device further comprises a contact judgment unit which judges whether a contact between at least a portion of the plurality of electrodes and the body surface of the subject is satisfactory or not.

According to this composition, if a contact defect has occurred between at least a portion of the plurality of electrodes and the body surface of the subject, then it is possible to detect that this contact defect has occurred.

Furthermore, desirably, the contact judgment unit comprises a first judgment unit which judges that a defect has occurred in the contact of both of the other pair of electrodes, when the average value is smaller than a predetermined first threshold value.

According to the composition described above, the first measurement unit performs voltage measurement a plurality of times in accordance with the current application unit switching the direction of the passed current, as described above, and the first judgment unit infers the state of contact resistance between the other pair of electrodes, in other words, the electrodes for voltage detection, and the body surface, from the average value of the plurality of measurement results. If the average value is abnormally small, then it is judged that a defect has occurred in the contact of both of the voltage detection electrodes.

Consequently, it is possible to respond appropriately, for instance, to the fact that a voltage detection electrode has become detached.

Moreover, desirably, the contact judgment unit comprises a second judgment unit which judges that a defect has occurred in the contact of one of the other pair of electrodes, when the average value is greater than a predetermined second threshold value.

According to the composition described above, if the average value of the plurality of measurement results is abnormally small as described above, then it is possible to judge that both of the voltage detection electrodes are floating, whereas if the average value is abnormally large, then the second judgment unit judges that a contact defect has occurred, for instance, that one of the voltage detection electrodes is not making adequate contact, or is disconnected, or that the skin is dry.

Furthermore, desirably, the contact judgment unit comprises a third judgment unit which judges that a defect has occurred in the contact of one of the pair of electrodes, if one of the measurement results corresponding respectively to the forward-direction current and the reverse-direction current is less than a predetermined first judgment threshold value and the other of the measurement results is greater than a second judgment threshold value which is greater than the first judgment threshold value.

According to the composition described above, measurement is carried out a plurality of times, as described above, and if the plurality of measurement results differ greatly and one is smaller than a predetermined first threshold value while the other is greater than a predetermined second threshold value, then the third judgment unit judges that a defect has occurred in the contact between one of the pair of electrodes, in other words, one of the pair of electrodes used to supply current, and the body surface.

Moreover, desirably, the third judgment unit judges that a defect has occurred in the contact of one electrode of the pair of electrodes, when a first measurement result which is the measurement result corresponding to the forward-direction current passed from the one electrode to the other electrode of the pair of electrodes is smaller than the first judgment threshold value, and a second measurement result which is the measurement result corresponding to the reverse-direction current passed from the other electrode to the one electrode is greater than the second judgment threshold value.

According to this composition, if a defect has occurred in the contact of one electrode of the pair of electrodes, which is the electrode where the forward-direction current flows out, then the occurrence of a contact defect in that electrode can be detected.

Furthermore, desirably, the third judgment unit judges that a defect has occurred in the contact of the other electrode of the pair of electrodes, when a first measurement result which is the measurement result corresponding to the forward-direction current passed from one electrode to the other electrode of the pair of electrodes is greater than the second judgment threshold value, and a second measurement result which is the measurement result corresponding to the reverse-direction current passed from the other electrode to the one electrode is smaller than the first judgment threshold value.

According to this composition, if a defect has occurred in the contact of the other electrode of the pair of electrodes, which is the electrode on the side where the reverse-direction current flows out, then the occurrence of a contact defect in that electrode can be detected.

Moreover, desirably, the contact judgment unit comprises a fourth judgment unit which judges that a balance of the other pair of electrodes is poor, when a difference between the respective measurement results is greater than a predetermined third threshold value.

According to this composition, measurement is carried out a plurality of times, as described above, and if the plurality of measurement results differ greatly and the difference therebetween is greater than a predetermined third threshold value, then the fourth judgment unit judges that the balance of contact between the other pair of electrodes, in other words, the voltage detection electrodes, and the body surface, is poor, for instance, that one of the electrodes is detached.

Moreover, desirably, the contact judgment unit comprises a fifth judgment unit which acquires a plurality of average values of respective measurement results while the connection is shut off, and judges that data is disrupted due to irregular breathing or body movements, when a difference between the maximum value and the minimum value of the plurality of average values is greater than a predetermined fourth threshold value.

According to the composition described above, when raising the measurement accuracy of the abdominal impedance, which is a very small value, by carrying out sampling a plurality of times, if the difference between the largest value and the smallest value is abnormally large, then the fifth judgment unit judges that the data has been disrupted due the occurrence of a defect in the electrode contact, as a result of irregular breathing, body movements, or the like.

Furthermore, desirably, the body fat measurement device further comprises an alarm generating unit (or an alarm generator) which issues an alarm in accordance with a judgment result of the contact judgment unit.

According to the composition described above, it is possible to issue an alarm by the alarm generating unit, if it is judged by the first to fifth judgment units that there is a defect in the state of contact between the electrodes and the body surface.

Consequently, the contact defect can be reported to a user, such as a subject or an examination technician, or the like, and the user can be made to reattach the electrodes, or the like, and thus carry out reliable and accurate measurement, easily.

Moreover, the body fat measurement device further comprises a fluctuation suppression unit which suppresses fluctuation in contact resistance between at least a portion of the electrodes and the body surface of the subject.

According to the composition described above, fluctuation occurs in the contact resistance between the electrodes and the body surface of the subject, due to the belt fastening, and the like. By providing means for suppressing this fluctuation, it is possible to detect the detachment of electrodes, and the like, and to carry out highly accurate measurement.

Furthermore, desirably, the fluctuation suppression unit comprises a variable resistor connected in series to at least a portion of the electrodes, and an adjustment unit which adjusts a resistance value of the variable resistor; and the adjustment unit adjusts the variable resistor connected to an electrode at which a contact defect is judged to have occurred, when the contact judgment unit judges that a defect has occurred in the contact of at least a portion of the electrodes.

According to the composition described above, when the state of contact between an electrode and the body surface is judged to be defective by the first to fifth judgment units, the fluctuation suppression unit adjusts the resistance value of the variable resistor which is connected in series with the electrode judged to be defective.

Therefore, if there is a problem with the contact resistance, it is possible to correct the contact resistance and to suppress fluctuation, by adjusting the variable resistance. By this means, accurate measurement can be performed readily, without reattaching the electrodes to the subject.

Moreover, the fluctuation suppression unit may comprise an actuator which drives at least a portion of the electrodes and a drive unit which drives the actuator; and the drive unit may adjust a state of contact by driving an electrode at which a contact defect is judged to have occurred, by means of the actuator, when the contact judgment unit judges that a defect has occurred in the contact of at least a portion of the electrodes.

According to the composition described above, if it is judged by the first to fifth judgment units that there is a defect on the state of contact between an electrode and the body surface, then the fluctuation suppression unit adjusts the contact resistance by driving the actuator provided on the electrode judged to have an abnormality, so as to push or pull the electrode, for instance.

Consequently, if there is a problem with the contact resistance, it is possible to suppress fluctuation by driving the actuator to adjust the contact between the electrodes and the body surface.

Furthermore, desirably, the isolating unit is an electrical switch.

According to the composition described above, by using an electrical switch such as a semiconductor switch element, as the isolating unit, the signal wire can readily be shut off automatically, without the subject being aware.

Moreover, in the body fat measurement device according to the present disclosure, the isolating unit may be a mechanical switch.

According to the composition described above, it is possible to shut off the signal wire at low cost, by using a mechanism switch that can be operated manually, as the isolating unit.

The body fat measurement device according to the present disclosure is a belt-type body fat measurement device in which, as described above, a plurality of electrodes are placed in contact with a body surface of a subject, from a belt wrapped around the abdomen of a subject, a predetermined current is passed by a current application unit (or a current applier) between a pair of electrodes at the center of the abdomen (navel) and the center of the back (spine) of the subject, of the plurality of electrodes, the voltage generated at the front and rear of a side of the subject during passage of the current is measured by a first measurement unit (or a first measurer), a calculation unit (or a calculator) determines an abdominal impedance from the measurement result of the first measurement unit, and an amount of body fat is calculated from the abdominal impedance, by desirably taking account also of other parameters, such as gender, weight, abdominal circumference, and the like, a second measurement unit (or a second measurer) which is capable of measuring another parameter which is different to the abdominal impedance and which can assist in the calculation of the amount of body fat being provided on the belt. In this, for the purpose of usability and costs, and the like, if a cable is used, in which first core wires that respectively connect the current calculation unit with a pair of electrodes corresponding to the first measurement unit and second core wires which connect the second measurement unit with the calculation unit to which the measurement result from the second measurement unit is input, are provided inside the same insulating coating (are formed in an integrated fashion), then an isolating unit (or an isolator) is provided between the second core wires and the calculation unit, and the line-to-line capacitance of the second core wires is isolated by this isolating unit during measurement of the abdominal impedance.

Therefore, even if a second measurement unit which is capable of measuring another parameter which is different to the abdominal impedance and which can assist in the calculation of the abdominal impedance is provided on the same belt, it is still possible to restrict decline in the measurement accuracy of the abdominal impedance, in other words, the measurement accuracy of a very small voltage.

This application is based on Japanese Patent Application No. 2009-174648 filed on 27 Jul. 2009, the contents of which are hereby incorporated in the present application.

The concrete embodiments or examples given in the description of the embodiments of the present disclosure are merely intended to clarify the technical contents of the present disclosure and the present disclosure is not to be interpreted in a narrow sense as limited to these examples only, but rather can be implemented with various modifications, within the spirit of the disclosure and the claims which are indicated below.

The invention claimed is:

1. A body fat measurement device, comprising:
a belt configured to be wrapped around an abdomen of a subject;
a plurality of electrodes which are provided on the belt and configured to contact a body surface of the subject;
a current applier which passes a predetermined current between a pair of electrodes of the plurality of electrodes;
a first measurer which measures a voltage between another pair of electrodes, of the plurality of electrodes, while the current is passed between the pair of electrodes by the current applier;
a calculator which calculates an abdominal impedance of the subject on the basis of the voltage measured by the first measurer and calculates an amount of body fat of the subject by using the calculated abdominal impedance;
a second measurer which measures a parameter other than the abdominal impedance and outputs a signal indicating the measured parameter to the calculator;
a cable in which a first core wire which connects between at least one of the current applier and the pair of electrodes, and the first measurer and the another pair of electrodes, and a second core wire which connects the second measurer and the calculator are provided inside a same insulating coating; and
an isolator which can shut off a connection between the second core wire and the calculator, wherein
the calculator shuts off the connection between the second core wire and the calculator by the isolator, during measurement of the abdominal impedance, acquires the voltage measured by the first measurer while the connection is shut off, and calculates the abdominal impedance on the basis of the acquired voltage.

2. The body fat measurement device according to claim 1, wherein the second measurer measures an abdominal circumference of the subject as the measured parameter.

3. The body fat measurement device according to claim 1, wherein the pair of electrodes are metal electrodes configured to be provided in a center of the abdomen and a center of the back of the subject, and the another pair of electrodes are gel electrodes which are configured to be attached to front and rear sides of the subject.

4. The body fat measurement device according to claim 1, wherein the pair of electrodes are metal electrodes configured to be provided in a center of the abdomen and a center of the back of the subject, and the another pair of electrodes are metal electrodes which are configured to be attached to front and rear sides of the subject.

5. The body fat measurement device according to claim 1, wherein
the current applier successively passes a current in a forward direction and a current in a reverse direction, the forward direction and the reverse direction being mutually opposite directions as a direction of a current passed between the pair of electrodes is successively switched; and
the calculator calculates a first abdominal impedance as an impedance measurement result corresponding to the forward-direction current, on the basis of the voltage measured by the first measurer which corresponds to the forward-direction current while the connection is shut off, calculates a second abdominal impedance as an impedance measurement result corresponding to the reverse-direction current, on a basis of the voltage measured by the first measurer which corresponds to the reverse-direction current while the connection is shut off, and calculates the abdominal impedance on the basis of an average value of the first abdominal impedance and the second abdominal impedance.

6. The body fat measurement device according to claim 1, wherein the isolator is an electrical switch.

7. The body fat measurement device according to claim 1, wherein the isolator is a mechanical switch.

8. The body fat measurement device according to claim 1, wherein
the current applier successively passes a current in a forward direction and a current in a reverse direction, the forward direction and the reverse direction being mutually opposite directions as a direction of a current passed between the pair of electrodes is successively switched; and
the calculator calculates the abdominal impedance on a basis of an average value of respective measurement results of voltages measured by the first measurer which correspond respectively to the forward-direction current and the reverse-direction current while the connection is shut off.

9. The body fat measurement device according to claim 8, further comprising a contact determiner which judges whether a contact between at least a portion of the plurality of electrodes and the body surface of the subject is satisfactory or not.

10. The body fat measurement device according to claim 9, wherein the contact determiner comprises a first determiner which judges that a defect has occurred in the contact of both of the another pair of electrodes, when the average value is smaller than a predetermined first threshold value.

11. The body fat measurement device according to claim 9, wherein the contact determiner comprises a second determiner which judges that a defect has occurred in the contact of one of the another pair of electrodes, when the average value is greater than a predetermined second threshold value.

12. The body fat measurement device according to claim 9, wherein the contact determiner comprises a fourth determiner which judges that a balance of the another pair of electrodes is poor, when a difference between the respective measurement results is greater than a predetermined third threshold value.

13. The body fat measurement device according to claim 9, wherein the contact determiner comprises a fifth determiner which acquires a plurality of average values of respective measurement results while the connection is shut off, and judges that data is disrupted due to irregular breathing or body movements, when a difference between a maximum value and a minimum value of the plurality of average values is greater than a predetermined fourth threshold value.

14. The body fat measurement device according to claim 9, further comprising an alarm generator which issues an alarm in accordance with a judgment result of the contact determiner.

15. The body fat measurement device according to claim 9, wherein the contact determiner comprises a third determiner which judges that a defect has occurred in the contact of one of the pair of electrodes, when one of the measurement results corresponding respectively to the forward-direction current and the reverse-direction current is less than a predetermined first judgment threshold value and the other of the measurement results is greater than a second judgment threshold value which is greater than the first judgment threshold value.

16. The body fat measurement device according to claim 15, wherein the third determiner judges that a defect has occurred in the contact of one electrode of the pair of electrodes, when a first measurement result which is the measurement result corresponding to the forward-direction current passed from the one electrode to the other electrode of the pair of electrodes is smaller than the first judgment threshold value, and a second measurement result which is the measurement result corresponding to the reverse-direction current passed from the other electrode to the one electrode is greater than the second judgment threshold value.

17. The body fat measurement device according to claim 15, wherein the third determiner judges that a defect has occurred in the contact of the other electrode of the pair of electrodes, when a first measurement result which is the measurement result corresponding to the forward-direction current passed from one electrode to the other electrode of the pair of electrodes is greater than the second judgment threshold value, and a second measurement result which is the measurement result corresponding to the reverse-direction current passed from the other electrode to the one electrode is smaller than the first judgment threshold value.

18. The body fat measurement device according to claim 9, further comprising a fluctuation suppressor which suppresses fluctuation in contact resistance between at least a portion of the electrodes and the body surface of the subject.

19. The body fat measurement device according to claim 18, wherein
the fluctuation suppressor comprises a variable resistor connected in series to at least a portion of the electrodes, and an adjuster which adjusts a resistance value of the variable resistor; and
the adjuster adjusts the variable resistor connected to an electrode at which a contact defect is judged to have occurred, when the contact determiner judges that a defect has occurred in the contact of at least a portion of the electrodes.

20. The body fat measurement device according to claim 18, wherein
the fluctuation suppressor comprises an actuator which drives at least a portion of the electrodes and a drive which drives the actuator; and
the drive adjusts a state of contact by driving an electrode at which a contact defect is judged to have occurred, by actuation of the actuator, when the contact determiner judges that a defect has occurred in the contact of at least a portion of the electrodes.

* * * * *